(12) United States Patent
Choi et al.

(10) Patent No.: US 10,215,742 B2
(45) Date of Patent: Feb. 26, 2019

(54) ELECTRONIC DEVICE AND OPERATION METHOD THEREOF

(71) Applicant: Samsung Electronics Co., Ltd., Suwon-si (KR)

(72) Inventors: Jongchul Choi, Gyeonggi-do (KR); Soohyung Kim, Gyeonggi-do (KR); Byounguk Yoon, Gyeonggi-do (KR); Taeho Kim, Chungcheongbuk-do (KR); Hyoungwook Yi, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 227 days.

(21) Appl. No.: 14/615,305

(22) Filed: Feb. 5, 2015

(65) Prior Publication Data

US 2015/0219608 A1    Aug. 6, 2015

(30) Foreign Application Priority Data

Feb. 5, 2014    (KR) .......................... 10-2014-0013120

(51) Int. Cl.
| | |
|---|---|
| G01N 33/00 | (2006.01) |
| G06F 1/20 | (2006.01) |
| G06F 1/16 | (2006.01) |
| G06F 3/01 | (2006.01) |
| G06F 3/0346 | (2013.01) |

(52) U.S. Cl.
CPC ..... G01N 33/0004 (2013.01); G01N 33/0009 (2013.01); G06F 1/1658 (2013.01); G06F 1/1684 (2013.01); G06F 1/1694 (2013.01); G06F 3/017 (2013.01); G06F 3/0346 (2013.01); *H04M 2250/12* (2013.01)

(58) Field of Classification Search
CPC ....................... G01N 33/0004; G01N 33/0009
USPC ................................................ 73/23.3, 31.01
See application file for complete search history.

(56) References Cited

U.S. PATENT DOCUMENTS

| | | | | |
|---|---|---|---|---|
| 3,877,291 A | * | 4/1975 | Hoppesch | .......... G01N 33/4972 340/634 |
| 7,904,123 B2 | * | 3/2011 | Makihata | .............. B81B 7/0077 381/361 |

(Continued)

FOREIGN PATENT DOCUMENTS

| | | |
|---|---|---|
| EP | 2 733 484 A1 | 5/2014 |
| KR | 20-0221994 | 2/2001 |

(Continued)

OTHER PUBLICATIONS

Partial European Search Report dated Sep. 30, 2015 in connection with European Patent Application No. 15153823.8; 6 pages.

*Primary Examiner* — Daniel S Larkin

(57) ABSTRACT

The electronic device includes at least one sensor configured to detect air flow in from outside of the electronic device, and a plurality of openings formed in the electronic device. Further, the electronic device includes a duct formed between the at least one sensor and at least one of the plurality of openings. A method for operating an electronic device having at least one sensor configured to detect air flow in from outside includes detecting a motion of the electronic device by using a motion sensor, recognizing a pattern of the detected motion, and activating a foreign matter removing unit when the recognized pattern corresponds to a predefined first motion pattern.

11 Claims, 28 Drawing Sheets

(56) References Cited

U.S. PATENT DOCUMENTS

| | | | |
|---|---|---|---|
| 8,182,143 B2 | 5/2012 | Fleming et al. | |
| 8,329,096 B2 * | 12/2012 | Elrod | G01N 33/0004 422/3 |
| 8,524,501 B2 * | 9/2013 | Adams | G01N 29/022 422/88 |
| 2004/0081582 A1 * | 4/2004 | Brooke | G01N 33/497 422/62 |
| 2006/0058697 A1 * | 3/2006 | Mochizuki | A61B 5/0002 600/532 |
| 2010/0275683 A1 | 11/2010 | Jia | |
| 2013/0092029 A1 | 4/2013 | Morgan et al. | |
| 2013/0192338 A1 * | 8/2013 | Mayer | G01N 33/4972 73/23.3 |
| 2013/0244336 A1 * | 9/2013 | Mayer | G01N 33/0031 436/147 |
| 2014/0208829 A1 * | 7/2014 | Lechner | G01N 33/497 73/31.01 |
| 2014/0223996 A1 * | 8/2014 | Hunziker | G01N 33/0031 73/31.01 |
| 2014/0311209 A1 * | 10/2014 | Niederberger | G01K 15/007 73/1.06 |
| 2014/0366610 A1 * | 12/2014 | Rodriguez | G01N 33/497 73/23.3 |

FOREIGN PATENT DOCUMENTS

| | | |
|---|---|---|
| KR | 10-1006820 | 1/2011 |
| KR | 10-1111077 | 2/2012 |

\* cited by examiner

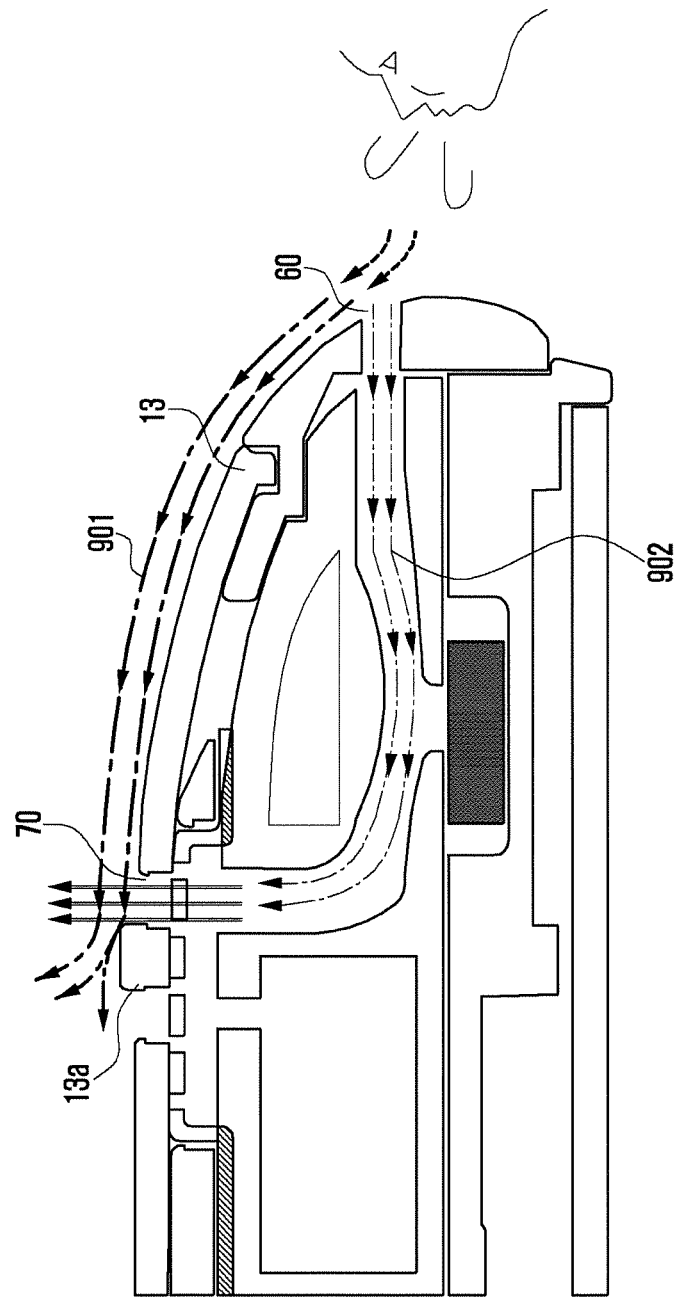

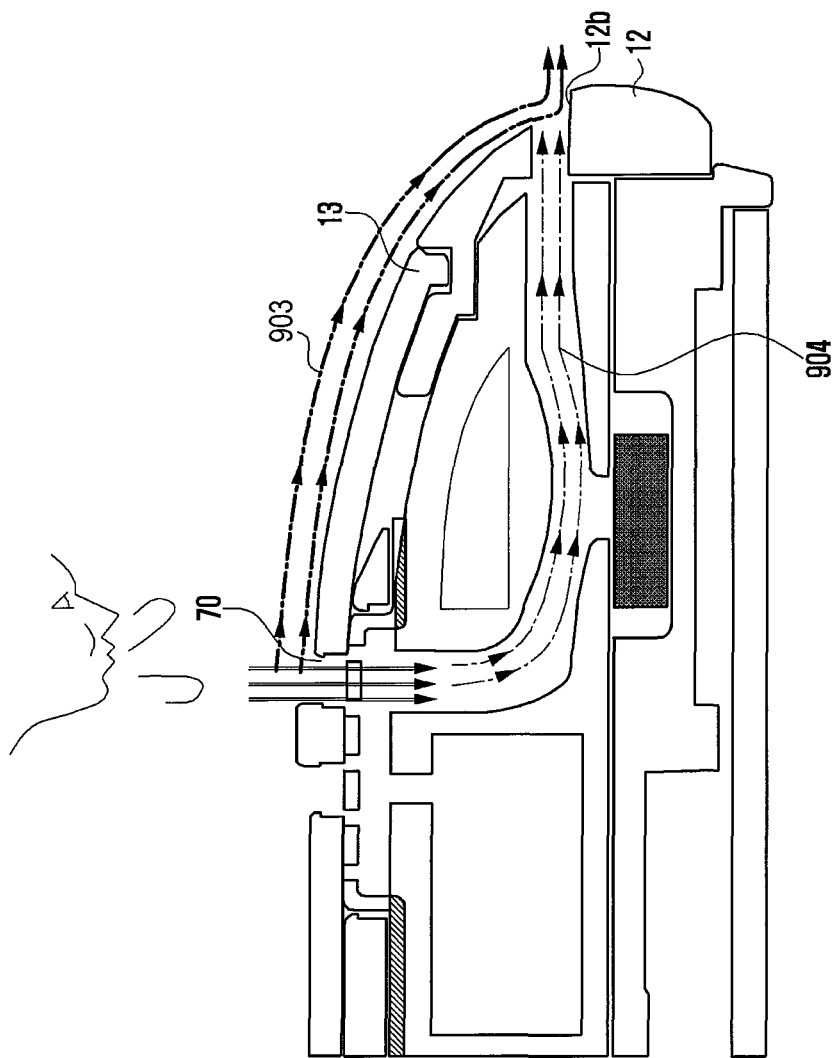

ELECTRONIC DEVICE AND OPERATION METHOD THEREOF

CROSS-REFERENCE TO RELATED APPLICATION AND CLAIM OF PRIORITY

The present application is related to and claims the benefit under 35 U.S.C. § 119(a) of a Korean patent application filed on Feb. 5, 2014 in the Korean intellectual property office and assigned serial No. 10-2014-0013120, the entire disclosure of which is hereby incorporated by reference.

TECHNICAL FIELD

Embodiments of the present disclosure relate to an electronic device having at least one sensor for detecting outside air flow and an operation method thereof.

BACKGROUND

With a remarkable growth of related technologies, a great variety of electronic devices are increasingly popularized in these days. Recent electronic devices offer various useful functions such as a call function, a music playback function, a digital camera function, an internet access function, a Bluetooth function, and the like.

In order to offer such functions, the electronic device may have many electronic components mounted therein. However, due to a slimmed-down structure for example, recent electronic devices have difficulty in securing a mounting space for electronic components.

Meanwhile, in recent years, the use of environmental sensors (e.g., a gas sensor, an odorant sensor, a temperature sensor, a humidity sensor, etc.) has been increased in electronic devices. Normally such environmental sensors are mounted in an isolated form to prevent undesirable effects by other electronic components. Therefore, conventional electronic devices have an additional separate substructure designed for isolating environmental sensors from other components while such environmental sensors are mounted together with other components in the same space. For this reason, conventional electronic devices having environmental sensors may be often confronted with difficulty in making slim and with a problem of low sensing accuracy.

Additionally, since it is required to mount environmental sensors at a position that allows an easy inflow or good sensing of outside air, conventional electronic devices may have a problem of limited design.

SUMMARY

To address the above-discussed deficiencies, it is a primary object to provide an electronic device, together with an operation method thereof, which has therein an environmental sensor without any additional separate substructure (e.g., an opening part).

Various embodiments of the present disclosure provide an electronic device, together with an operation method thereof, which has therein an environmental sensor installed in a duct structure for an air inflow through a plurality of opening parts without adding any separate substructure.

However, various embodiments of the present disclosure are not limited to cases of having no separate substructure. For example, in some cases, environmental sensors may have any separate substructure suitable for easily sensing outside air.

According to an embodiment of present disclosure, an electronic device includes at least one sensor configured to detect air flow from outside of the electronic device, a plurality of openings formed in the electronic device, and a duct formed between the at least one sensor and at least one of the plurality of openings.

According to an embodiment of present disclosure, an electronic device includes a display unit; a first case on which the display unit is mounted, and at least one sensor located bottom of a gap formed between the display unit and the first case and configured to detect air flow from outside of the electronic device through the gap.

According to an embodiment of present disclosure, an electronic device includes a cover including at least one hole therein and being in an opened or closed state with respect to one side of the electronic device, and at least one sensor associated with the cover and configured to detect air flow in from outside through the at least one hole.

According to an embodiment of present disclosure, an electronic device includes a first case on which a display unit is mounted, a second case combined with the first case and including a plurality of openings and a duct connected to the plurality of openings, a third case connected functionally to the electronic device and including at least one hole, and at least one sensor mounted on the third case and configured to detect outside air which flows in through the plurality of openings and the duct.

According to an embodiment of present disclosure, a method for operating an electronic device including at least one sensor configured to detect air flow in from outside may include detecting a motion of the electronic device by using a motion sensor, recognizing a pattern of the detected motion, and activating a foreign matter removing unit when the recognized pattern corresponds to a predefined first motion pattern.

According to an embodiment of present disclosure, a method for operating an electronic device including at least one sensor configured to obtain air which flows in from outside may include detecting a motion of the electronic device by using a motion sensor, recognizing a pattern of the detected motion; and activating the at least one sensor when the recognized pattern corresponds to a predefined motion pattern.

According to an embodiment of present disclosure, a method for operating an electronic device including at least one sensor configured to obtain air which flows in from outside may include determining whether a sound corresponding to an inflow of outside air is detected through a microphone; and activating the at least one sensor when the sound corresponding to the inflow of outside air is detected through the microphone.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIGS. 9A and 9B are cross-sectional views illustrating a duct structure of an electronic device in accordance with various embodiments of the present disclosure.

DETAILED DESCRIPTION

Figure 1:
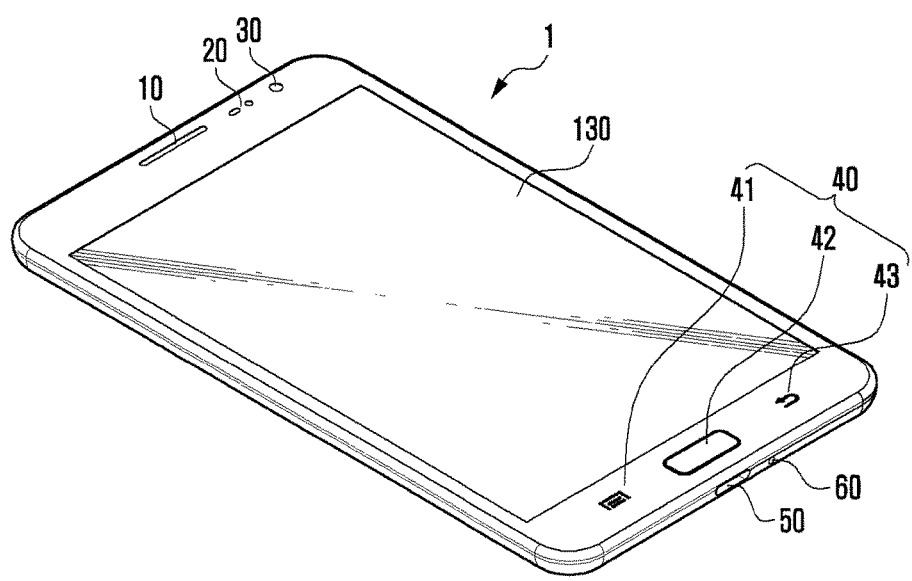
FIG. 1 is a perspective view illustrating a front side of an electronic device in accordance with various embodiments of the present disclosure.

FIGS. 1 through 26, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged electronic device. The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

The expressions such as "include" and "may include" which may be used in various embodiments of the present disclosure denote the presence of the disclosed functions, operations, and constituent elements and do not limit one or more additional functions, operations, and constituent elements. Additionally, in various embodiments of the present disclosure, the terms such as "comprise", "include", and/or "have" may be construed to denote a certain characteristic, number, step, operation, constituent element, component or a combination thereof, but may not be construed to exclude the existence of or a possibility of addition of one or more other characteristics, numbers, steps, operations, constituent elements, components or combinations thereof.

Furthermore, in various embodiments of the present disclosure, the expression "or" includes any and all combinations of the associated listed words. For example, the expression "A or B" may include A, may include B, or may include both A and B.

In various embodiments of the present disclosure, expressions including ordinal numbers, such as "first" and "second," etc., and/or the like, may modify various elements. However, such elements are not limited by the above expressions. For example, the above expressions do not limit the sequence and/or importance of the elements. The above expressions are used merely for the purpose to distinguish an element from the other elements. For example, a first user device and a second user device indicate different user devices although both of them the first user device and the second user device are user devices. For example, a first element could be termed a second element, and similarly, a second element could be also termed a first element without departing from the scope of the present disclosure.

In the case where according to which a component is referred to as being "connected" or "accessed" to other component, it should be understood that not only the component is directly connected or accessed to the other component, but also there may exist another component between them the component and the other component. Meanwhile, in the case where according to which a component is referred to as being "directly connected" or "directly accessed" to other component, it should be understood that there is no component therebetween. The terms used in the present disclosure are only used to describe specific various embodiments, and are not intended to limit the present disclosure. As used herein, the singular forms are intended to include the plural forms as well, unless the context clearly indicates otherwise. Singular forms are intended to include plural forms unless the context clearly indicates otherwise.

The term "unit" or "module", as used herein, may refer to a software or hardware component or device which performs certain tasks. A unit or module may be configured to reside on an addressable storage medium and configured to execute on one or more processors. Thus, a module or unit may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules/units may be combined into fewer components and modules/units or further separated into additional components and modules.

In various embodiments of present disclosure, an electronic device may be a device that involves an environmental sensor function. For example, an electronic device may be a smart phone, a tablet PC (Personal Computer), a mobile phone, a video phone, an e-book reader, a desktop PC, a laptop PC, a netbook computer, a PDA (Personal Digital Assistant), a PMP (Portable Multimedia Player), an MP3 player, a portable medical device, a digital camera, or a wearable device (e.g., an HMD (Head-Mounted Device) such as electronic glasses, electronic clothes, an electronic bracelet, an electronic necklace, an electronic appcessory, or a smart watch).

According to some embodiments, an electronic device may be a smart home appliance that involves a communication function. For example, an electronic device may be a TV, a DVD (Digital Video Disk) player, audio equipment, a refrigerator, an air conditioner, a vacuum cleaner, an oven, a microwave, a washing machine, an air cleaner, a set-top box, a TV box (e.g., Samsung HomeSync™, Apple TV™, Google TV™, etc.), a game console, an electronic dictionary, an electronic key, a camcorder, or an electronic picture frame.

According to some embodiments, an electronic device may be a medical device (e.g., MRA (Magnetic Resonance Angiography), MRI (Magnetic Resonance Imaging), CT (Computed Tomography), ultrasonography, etc.), a navigation device, a GPS (Global Positioning System) receiver, an EDR (Event Data Recorder), an FDR (Flight Data Recorder), a car infotainment device, electronic equipment for ship (e.g., a marine navigation system, a gyrocompass, etc.), avionics, security equipment, an industrial or home robot, an ATM (Automatic Teller's Machine), or a POS (Point of Sales).

According to some embodiments, an electronic device may be furniture or part of a building or construction having a communication function, an electronic board, an electronic signature receiving device, a projector, or various measuring instruments (e.g., a water meter, an electric meter, a gas meter, a wave meter, etc.). An electronic device disclosed herein may be one of the above-mentioned devices or any combination thereof. As well understood by those skilled in the art, the above-mentioned electronic devices are exemplary only and not to be considered as a limitation of present disclosure.

Now, an electronic device according to various embodiments of the present disclosure will be described with reference to the accompanying drawings. The term 'user' to be used herein can refer to a person or machine (e.g., an artificial intelligence apparatus or system) using an electronic device.

Figure 2:
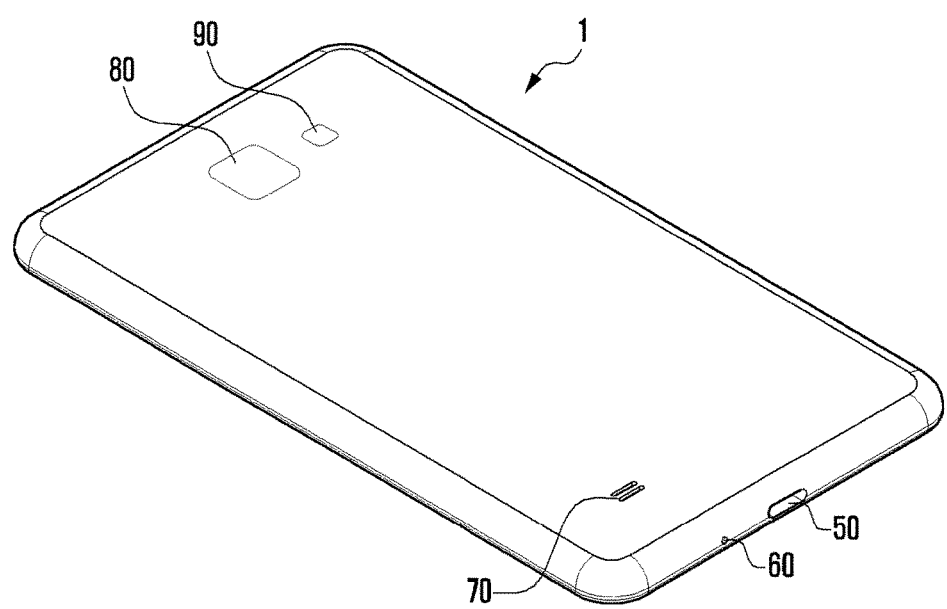
FIG. 2 is a perspective view illustrating a rear side of an electronic device in accordance with various embodiments of the present disclosure.
Figure 3:
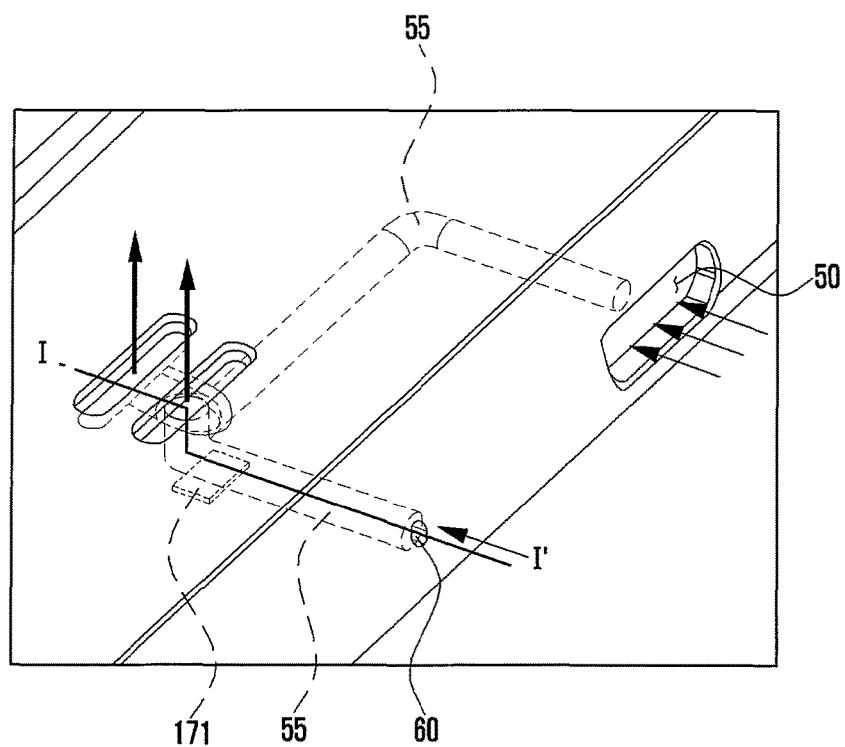
FIG. 3 is a perspective view illustrating a duct structure of an electronic device in accordance with various embodiments of the present disclosure.
Figure 4:
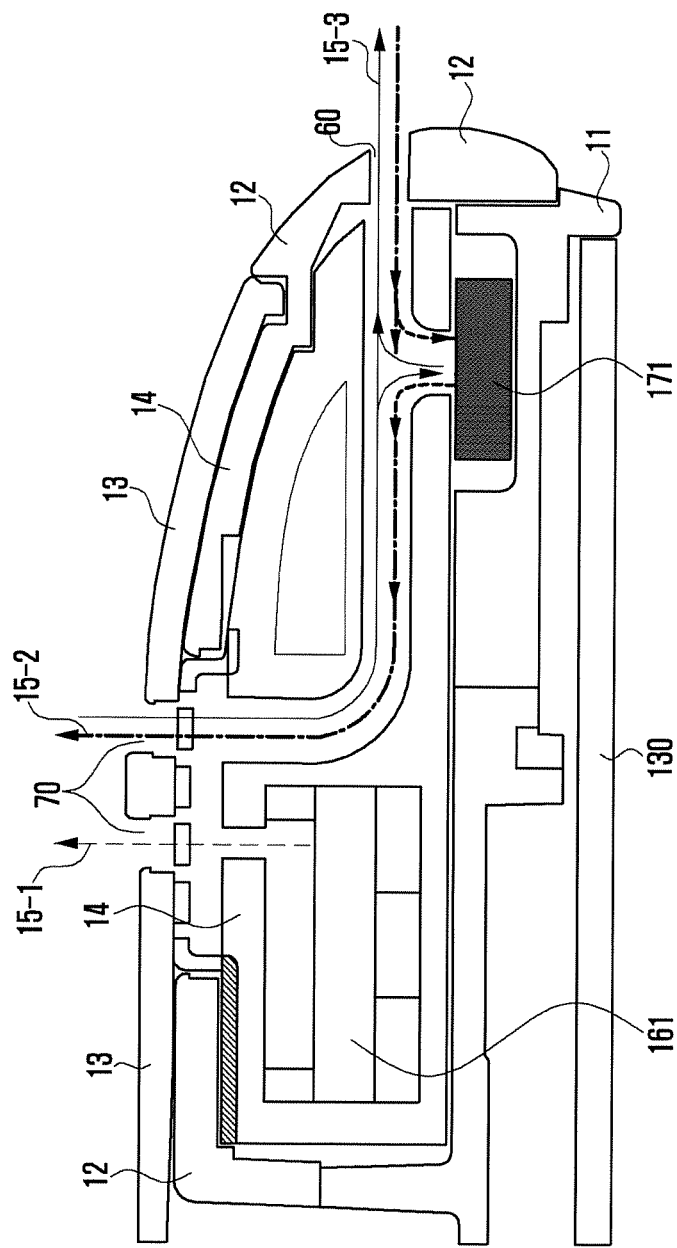
FIG. 4 is a cross-sectional view taken along the line A-A' in FIG. 3.
Figure 5:
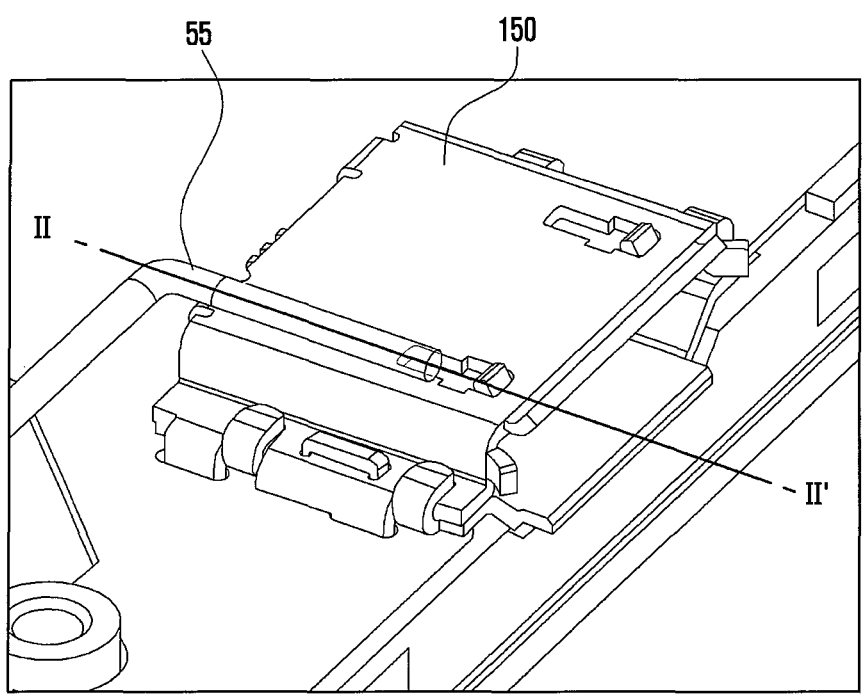
FIG. 5 is a perspective view illustrating a duct structure of an electronic device in accordance with various embodiments of the present disclosure.
Figure 6:
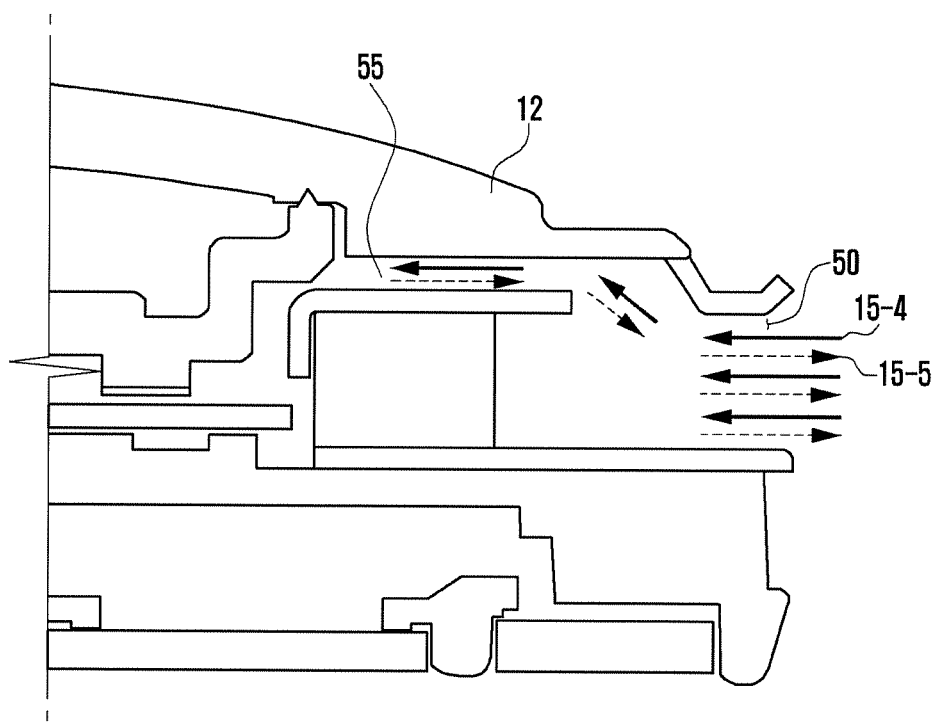
FIG. 6 is a cross-sectional view taken along the line B-B' in FIG. 5.

FIG. 1 is a perspective view illustrating a front side of an electronic device in accordance with various embodiments of the present disclosure. FIG. 2 is a perspective view illustrating a rear side of an electronic device in accordance with various embodiments of the present disclosure. FIG. 3 is a perspective view illustrating a duct structure of an electronic device in accordance with various embodiments of the present disclosure. FIG. 4 is a cross-sectional view taken along the line A-A' in FIG. 3. FIG. 5 is a perspective view illustrating a duct structure of an electronic device in accordance with various embodiments of the present disclosure. FIG. 6 is a cross-sectional view taken along the line B-B' in FIG. 5.

Referring to FIGS. 1 and 2, the electronic device 1 can be formed of a bar type, for example. This is, however, exemplary only and not to be considered as a limitation of the present disclosure. Alternatively, the electronic device 1 according to various embodiments can be formed of any other type such as a folder type, a slide type, or the like.

The electronic device 1 can include a receiver 10 for the output of a call sound, an illuminance sensor 20, a front camera 30, and a function key 40. The function key 40 can have at least one of a menu key 41, a home key 42, a cancel key 43, and a volume key (not shown). The menu key 41 or the cancel key 43 can be a touch-type mechanical key, and the home key 42 or the volume key (not shown) can be a button-type mechanical key. However, this is exemplary only and not to be considered as a limitation. For example, the menu key 41, the home key 42 and the cancel key 43 can be formed of one or combination of a touch type and a button type. Also, the menu key 41, the home key 42, the cancel key 43 and the volume key (not shown) can be formed of a non-mechanical key, e.g., a soft key offered through a functionally connected display.

The electronic device 1 can include an interface unit hole 50 and a microphone hole 60 on a bottom side thereof. Also, the electronic device 1 can include, at a rear side thereof, a speaker hole 70 for the output of audio signal from a sound output module (not shown), a rear camera 80 for capturing an image or recording a video, and a flash 90 for offering light for the rear camera 80.

The electronic device 1 can include, at a front side thereof, a display unit 130 (e.g., LCD (Liquid Crystal Display), AMOLED (Active Matrix Organic Light Emitting Diode)).

The shape of the electronic device 1 shown in FIGS. 1 and 2 is exemplary only and not to be considered as a limitation of the present disclosure.

Next referring to FIGS. 3 and 4, the electronic device 1 in an embodiment of present disclosure can include opening parts (e.g., the interface unit hole 50, the microphone hole 60, the speaker hole 70) formed on a case or body thereof. Additionally, the electronic device 1 can include a duct 55 formed to guide a flow of air between such opening parts. For example, air which flows in through one of the opening parts can move along the duct 55 and then flow out through one of the others.

The electronic device 1 can include an environmental sensor 171 for sensing environmental information. For example, the environmental sensor 171 can include, but not limited to, a temperature sensor, a humidity sensor, an odorant sensor, a gas sensor, or the like.

The environmental sensor 171 can be located near (e.g., under) the duct 55 and thereby easily obtain outside air which passes through the duct 55. By obtaining air flow in from the outside of the electronic device 1, the environmental sensor 171 can analyze external environmental information. For example, in various embodiments, the environmental sensor 171 of the electronic device 1 can obtain air flow in through the opening parts (e.g., the interface unit hole 50, the microphone hole 60, the speaker hole 70) formed on a case of the electronic device 1 and then analyze environmental information. Alternatively, in some embodiment, the environmental sensor 171 can obtain outside air, and the control unit (not shown) can analyze the obtained air.

The opening parts (e.g., the interface unit hole 50, the microphone hole 60, the speaker hole 70, etc.) of the electronic device 1 can perform the function of an inflow hole or an outflow hole for air supplied to the environmental sensor 171.

Specifically, referring to FIG. 4, the electronic device 1 according to various embodiments can include the first case 11 having the display unit 130 attached thereto, the second case 12 combined with the first case 11, and the third case 13 detachably combined with the second case 12. For example, the first case 11 can be a front case, the second case 12 can be a rear case, and the third case 13 can be a cover case (e.g., a battery cover).

According to various embodiments, a carrier 14 for holding a speaker 161 therein can be located between the second and third cases 12 and 13. For example, the second and third cases 12 and 13 can have the microphone hole 60 and the speaker hole 70 respectively formed thereon. The carrier 14 can have the duct 55 formed therein.

As indicated by the first arrow 15-1 in FIG. 4, sound can be outputted from the speaker 161 through the speaker hole 70.

As indicated by the second arrow 15-2 in FIG. 4, the outside air can flow into the electronic device 1 through the microphone hole 60. The inflowing air can be supplied to the environmental sensor 171 through the duct 55 and then flow out through the speaker hole 70. Contrary to this, the outside air can flow in through the speaker hole 70 and flow out through the microphone hole 60 as indicated by the third arrow 15-3.

Referring to FIGS. 5 and 6, an interface unit 150 (e.g., an interface connector) mounted in the electronic device 1 can have a hole 50 formed at an upper part thereof. The outside air can flow in the electronic device 1 through the hole 50 of the interface unit 150 and through a gap between the interface unit 150 and the second case 12 or the carrier 14. Therefore, the electronic device 1 can have the duct 55 formed along such a gap between the interface unit 150 and the second case 12 or the carrier 14.

As indicated by the fourth arrow 15-4 shown in FIG. 6, the inflowing air can be supplied to the duct 55 through the interface unit hole 50 and then flow out through the microphone hole 60 and the speaker hole 70. Contrary to this, as indicated by the fifth arrow 15-5, the air flowing in through the microphone hole 60 and the speaker hole 70 can be supplied to the duct 55 and then flow out through the interface unit hole 50. The environmental sensor can obtain the outside air through the duct 55 and analyze environmental information.

As discussed above in various embodiments, an exact and prompt sensing of external environments is possible through the environmental sensor 171 together with the inflow and outflow holes. Additionally, the utilization of opening parts, as the inflow and outflow holes, formed normally on the case of the electronic device 1 can allow a slimmer structure and a freer design of the electronic device 1.

However, various embodiments of the present disclosure are not limited to instances of having no separate substructure. For example, in some instances, environmental sensors can have any separate substructure suitable for easily sensing the outside air.

Figure 7:
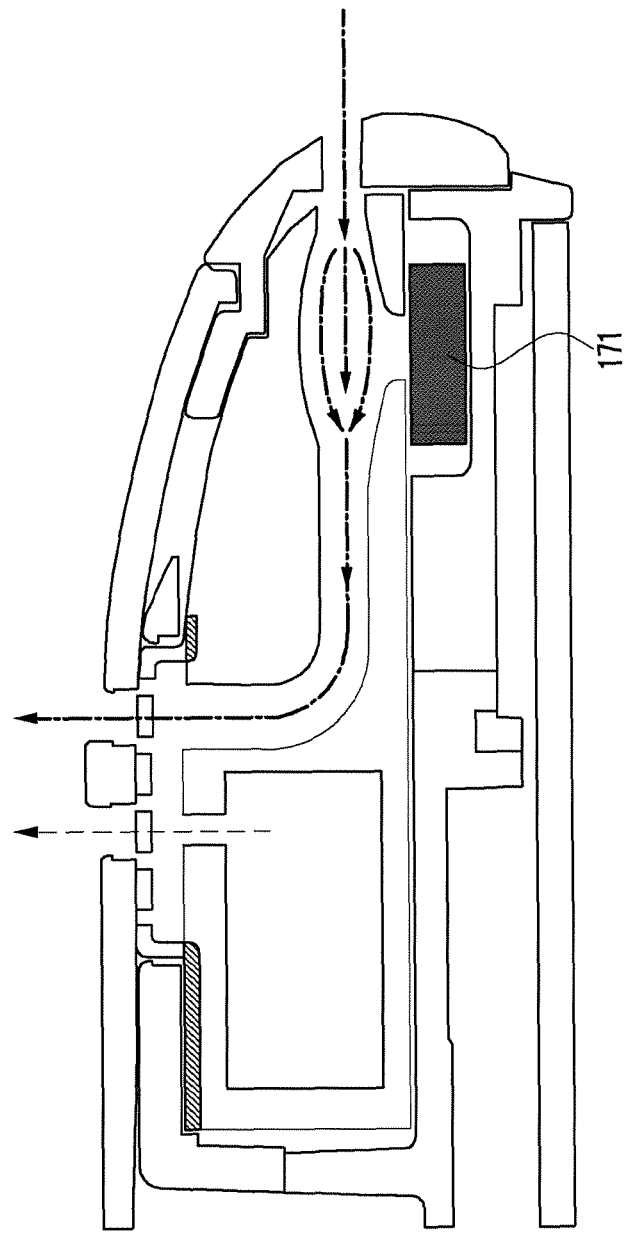
FIG. 7 is a cross-sectional view illustrating a duct structure of an electronic device in accordance with various embodiments of the present disclosure.

FIG. 7 is a cross-sectional view illustrating a duct structure of an electronic device in accordance with various embodiments of the present disclosure.

Referring to FIG. 7, the duct according to various embodiments can have an internal space which becomes broader at a position of the environmental sensor 171. When air flows from a narrow portion to a broad portion in the internal space, a flow velocity of the air can be decreased at the broad portion. This can allow the environmental sensor 171 to obtain the flowing-in air for an increased time. It is therefore possible for the environmental sensor 171 to exactly measure the flowing-in air.

Figure 8:
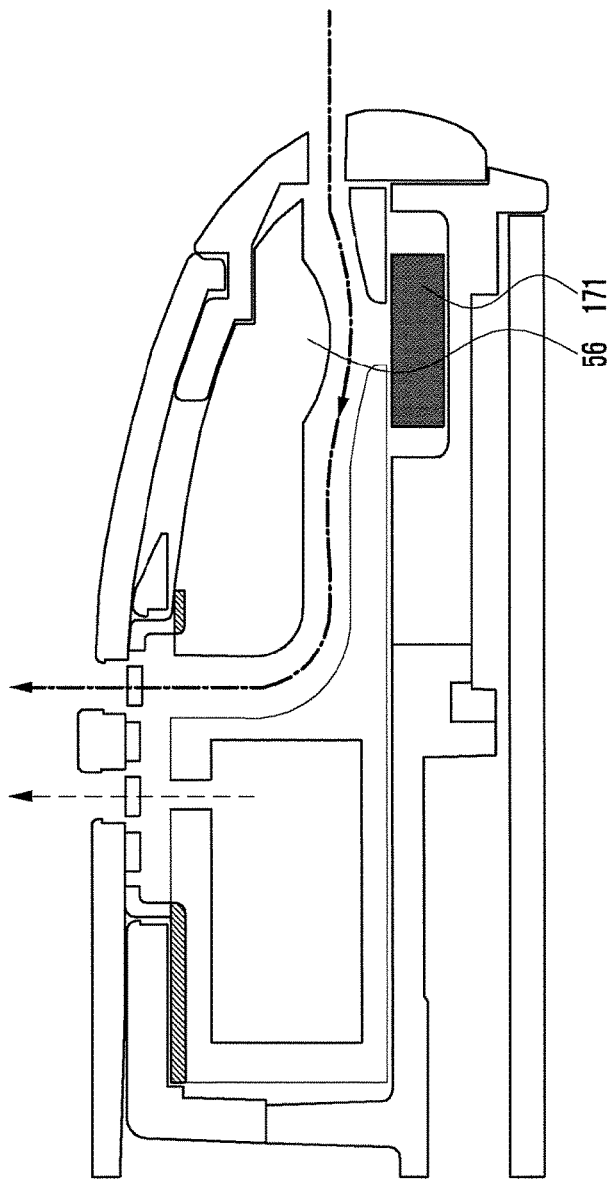
FIG. 8 is a cross-sectional view illustrating a duct structure of an electronic device in accordance with various embodiments of the present disclosure.

FIG. 8 is a cross-sectional view illustrating a duct structure of an electronic device in accordance with various embodiments of the present disclosure.

Referring to FIG. 8, the duct can have a shape for allowing a change in a moving direction of air at a position of the environmental sensor 171. For example, as shown in FIG. 8, the duct can have therein a protrusion 56 which protrudes toward the environmental sensor 171 from the opposite side of the environmental sensor 171. The protrusion 56 can allow the air to move in a direction changed toward the environmental sensor 171. This can increase a flow velocity or pressure of the air flow toward the environmental sensor 171. It is therefore possible for the environmental sensor 171 to exactly and promptly measure or analyze the inflowing air.

According to various embodiments, the internal space of the duct can become narrower at a position of the environmental sensor 171 due to the protrusion 56. At this time, a flow velocity or pressure of the flowing-in air can be increased, so that the environmental sensor 171 can exactly and promptly measure or analyze the inflowing air.

Although FIG. 8 shows a change in a moving direction of air by the protrusion 56, various embodiments are not limited to this. Alternatively, the duct can be formed to be biased to the environmental sensor 171 from the inflow hole. This biased duct structure can be applied to all cases in which the width of the duct is unchanged, increased or decreased. Further, although FIG. 8 shows a streamlined shape to this protrusion 56, various embodiments are not limited to this. Alternatively, the protrusion can have any other shape (e.g., a triangular shape).

FIGS. 9A and 9B are cross-sectional views illustrating a duct structure of an electronic device in accordance with various embodiments of the present disclosure.

Referring to FIGS. 9A and 9B, in various embodiments, the electronic device 1 can reduce the time required for the environmental sensor 171 to obtain the outside air by using a difference in atmospheric pressure. For example, when a user blows air into the microphone hole 60 as shown in FIG. 9A, the air can partially flow into the electronic device 1 through the microphone hole 60 and partially flow along an outer surface of the electronic device 1. At this time, air 902 which flows along the inside of the electronic device 1 can have a lower speed than that of air 901 which flows along the outer surface of the electronic device 1. Additionally, an atmospheric pressure around the speaker hole 70 becomes smaller than an internal atmospheric pressure in the electronic device 1. Therefore, a difference in atmospheric pressure occurs between the inside and outside of the electronic device 1, and the flow of internal air becomes faster. As a result, an increase in a flow velocity of air allows a prompt supply of the outside air to the environmental sensor 171. Further, the amount of the outside air obtained by the environmental sensor 171 for a given time can be also increased. Like so, in some embodiments, the environmental sensor 171 can perform a prompt measurement of external environments through a faster inflow and delivery of outside air, and also quickly offer measured environmental information to the electronic device 1.

In some embodiments, as shown in FIG. 9A, the third case 13 can have the first bump 13a formed around the speaker hole 70. The first bump 13a can change a direction of air 901 which flows along the outer surface. For example, the air 901 flowing along the outer surface can have a direction changed by the first bump 13a and being similar to that of air 902 flowing out from the inside of the electronic device 1. When such air flows having similar directions are merged, a flow velocity of the merged air can be increased and thus a flow velocity of the air 902 flowing along the inside of the electronic device 1 can also be increased.

In some embodiments, as shown in FIG. 9B, when a user blows air into the speaker hole 70, the air can partially flow in the electronic device 1 through the speaker hole 70 and partially flow along an outer surface of the electronic device 1. At this time, air 904 which flows along the inside of the electronic device 1 can have a lower speed than that of air 903 which flows along the outer surface of the electronic device 1. Additionally, an atmospheric pressure around the microphone hole 60 becomes smaller than an internal atmospheric pressure in the electronic device 1. Therefore, a difference in atmospheric pressure occurs between the inside and outside of the electronic device 1, and the flow of internal air becomes faster.

Like so, in some embodiments, the environmental sensor 171 can perform a prompt measurement of external environments through a faster inflow and delivery of outside air, and also quickly offer measured environmental information to the electronic device 1.

In some embodiments, as shown in FIG. 9B, the second case 12 can have the second bump 12b formed at the bottom of the microphone hole 60. Air 903 flowing along the outer surface can have a direction changed by the second bump 12b and being similar to that of air 904 flowing out through the microphone hole 60. When such air flows having similar directions are merged, a flow velocity of the merged air can be increased and thus a flow velocity of the air 904 in the electronic device 1 can also be increased.

Figure 10:
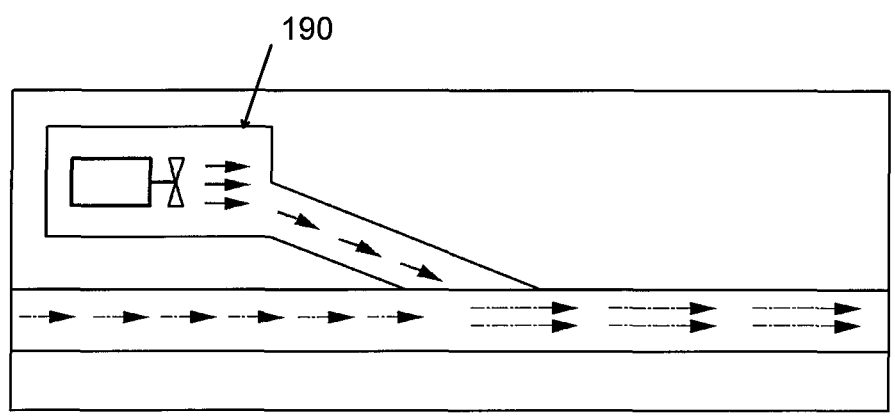
FIG. 10 is a schematic view illustrating a duct structure of an electronic device in accordance with various embodiments of the present disclosure.
Figure 11:
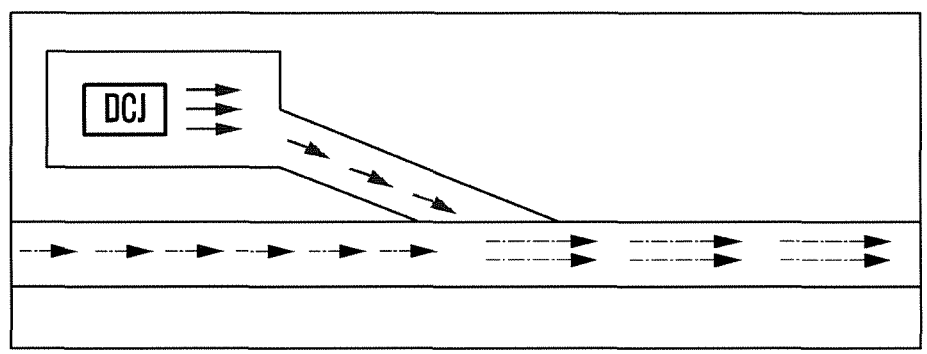
FIG. 11 is a schematic view illustrating a duct structure of an electronic device in accordance with various embodiments of the present disclosure.

FIG. 10 is a schematic view illustrating a duct structure of an electronic device in accordance with various embodiments of the present disclosure. FIG. 11 is a schematic view illustrating a duct structure of an electronic device in accordance with various embodiments of the present disclosure.

Referring to FIGS. 10 and 11, the electronic device according to various embodiments can further have an auxiliary unit for increasing a flow velocity of air in the duct. The auxiliary unit can be a vibration motor or an actuator such as Dual piezoelectric Cooling Jets (DCJ). For example, by connecting a fan with a head of the vibration motor as shown in FIG. 10 or by using the DCJ as shown in FIG. 11, a flow velocity of air can be increased for prompt sensing. Herein, the DCJ is a cooling system which employs a recently developed ultra-thin piezoelectric device. Based on piezoelectric technique, the DCJ may generate the flow of air without using a bearing and a DC motor. A detailed description about the DCJ will be omitted herein. Using this auxiliary unit, the electronic device according to various embodiments may increase a flow velocity of air in the duct.

Figure 12:
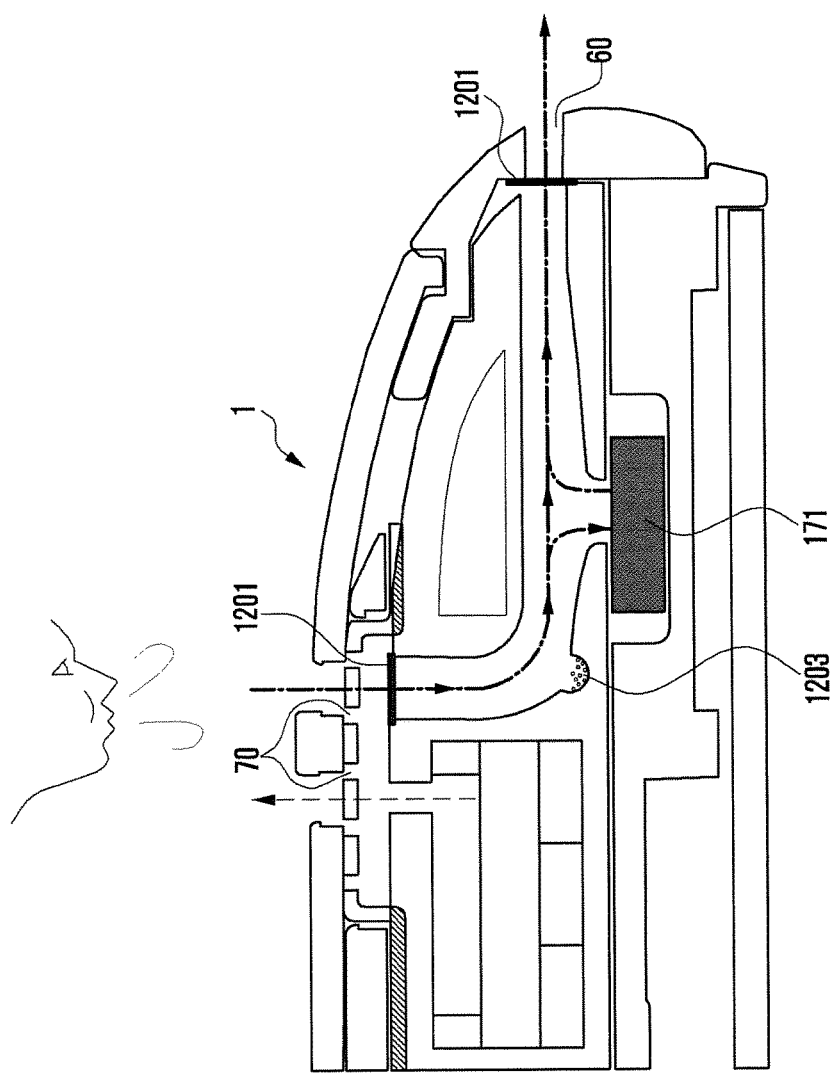
FIG. 12 is a cross-sectional view illustrating a duct structure of an electronic device in accordance with various embodiments of the present disclosure.

FIG. 12 is a cross-sectional view illustrating a duct structure of an electronic device in accordance with various embodiments of the present disclosure. Referring to FIG. 12, the duct according to various embodiments may have at least one of a protective member 1201 (e.g., a mesh or waterproof mesh) for preventing the inflow of foreign matter (e.g., dust, spit, etc.) and a receptacle, or a hollow part 1203 for storing a deposit of foreign matter. Specifically, the protective member 1201 may be attached to the entrance of the duct. The hollow part 1203 may be formed at a curved position where a flow direction of air is changed. For example, the hollow part 1203 may be formed at the opposite side of the speaker hole 70. This is to allow foreign matter flowing in through the speaker hole 70 to be deposited in the hollow part 1203 by gravity while the electronic device 1 is in a horizontal state (i.e., the display unit is horizontal on the ground). Also, this is to allow foreign matter such as spit to be deposited in the hollow part 1203 before arriving at the environmental sensor 171.

According to various embodiments, the hollow part 1203 may be formed near the opening part through which air is likely to be supplied (e.g., by user's blowing). For example, if there is a possibility of supplying air through the speaker hole 70 as shown in FIG. 12, the hollow part 1203 may be located around the speaker hole 70.

Figure 13:
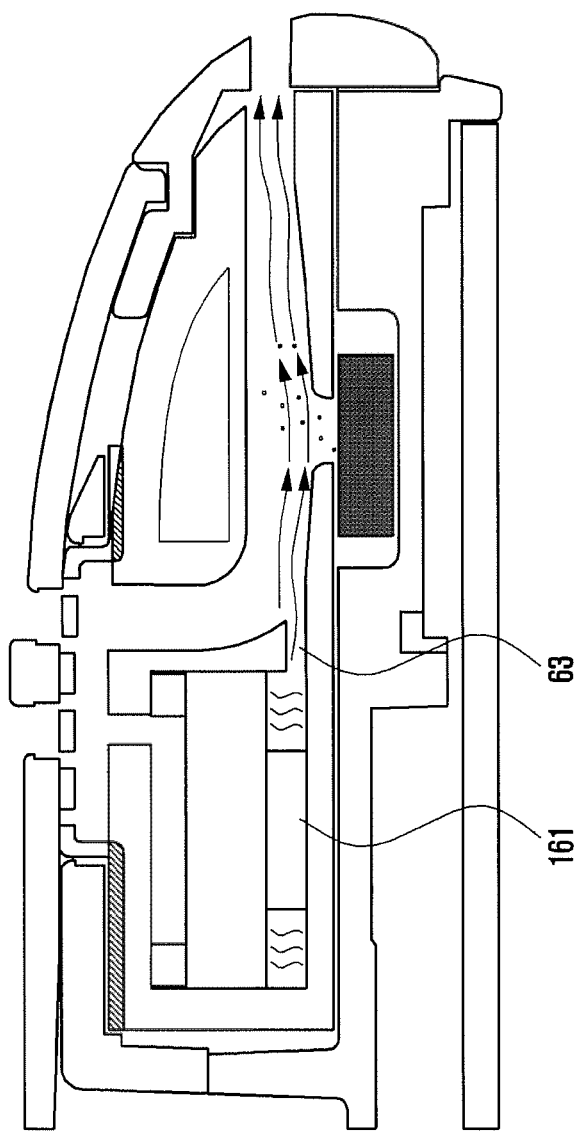
FIG. 13 is a cross-sectional view illustrating a method for removing foreign matter by using a speaker in accordance with various embodiments of the present disclosure.

FIG. 13 is a cross-sectional view illustrating a method for removing foreign matter by using a speaker in accordance with various embodiments of the present disclosure.

Referring to FIG. 13, the electronic device according to various embodiments may remove foreign matter from the surroundings of the environmental sensor 171 by using the speaker 161. Specifically, a hole 63 may be formed between the speaker 161 and the duct. When the speaker 161 outputs an audio signal, the speaker 161 vibrates. This vibration may cause an air flow toward the duct through the hole 63. Then this air flow may exhaust foreign matter around the environmental sensor 171 to the outside.

In some embodiments, the vibration motor or the actuator such as the DCJ may be used instead of the speaker 161 so as to remove foreign matter. For example, when the removal of foreign matter is required, the electronic device may activate the actuator. The activated actuator may move air in a specific direction (e.g., outward), and foreign matter may be exhausted to the outside by a movement of air.

Figure 14:
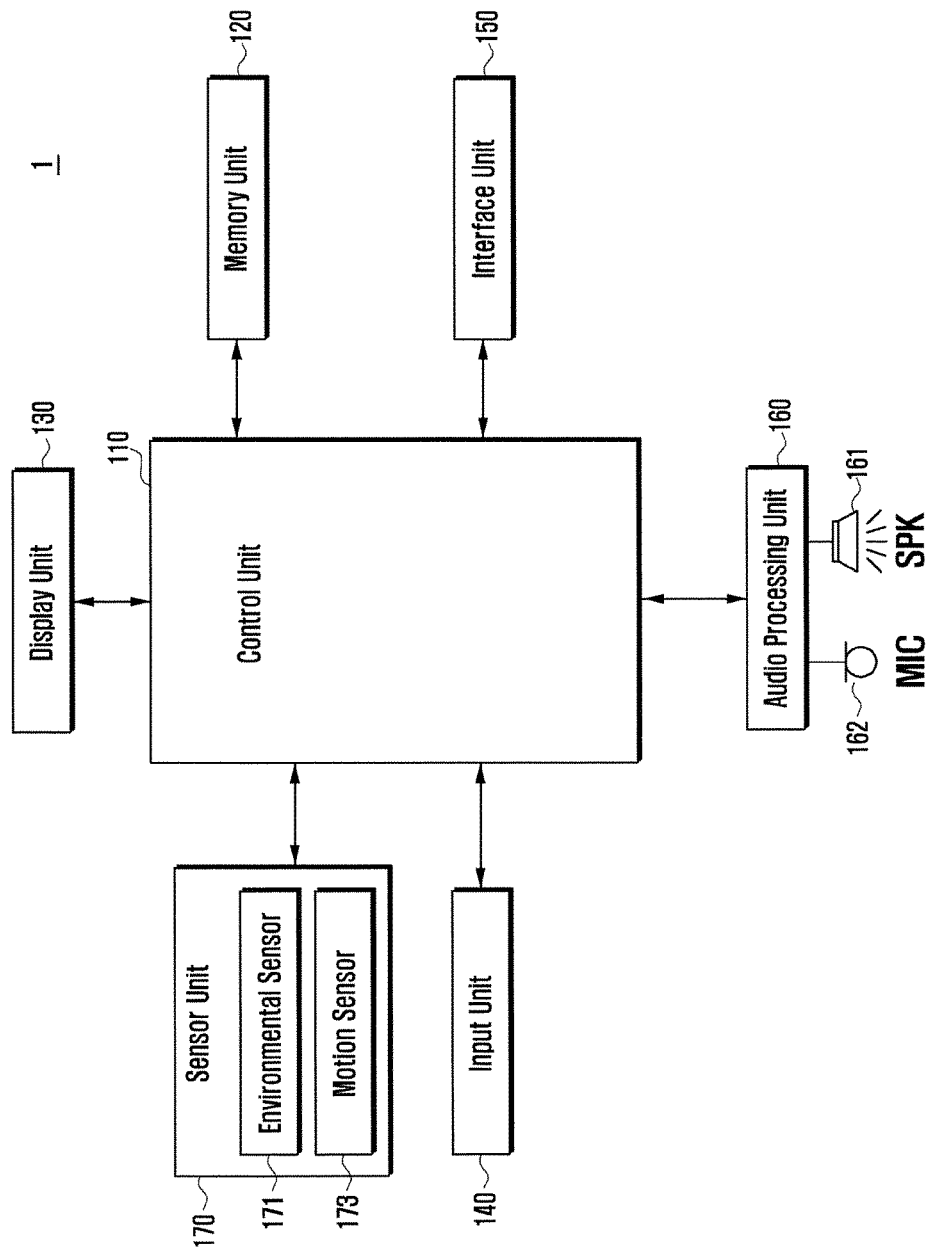
FIG. 14 is a block diagram illustrating an electronic device in accordance with various embodiments of the present disclosure.

FIG. 14 is a block diagram illustrating an electronic device in accordance with various embodiments of the present disclosure. Referring to FIG. 14, the electronic device 1 according to various embodiments may include a control unit 110, a memory unit 120, a display unit 130, an input unit 140, an interface unit 150, an audio processing unit 160, and a sensor unit 170.

The display unit 130 may display thereon various types of information, including various menus of the electronic device 1, entered by a user or to be offered to a user. For example, the display unit 130 may offer various screens associated with the use of the electronic device 1, such as an idle screen, a menu screen, a webpage screen, a call screen, and the like. Additionally, when a motion of the electronic device 1 corresponding to a predefined motion pattern is detected, the display unit 130 may display thereon a popup window that shows a query about whether to activate the speaker 161 so as to remove foreign matter. The display unit 130 may be formed of Liquid Crystal Display (LCD), Organic Light Emitting Diode (OLED), Active Matrix OLED (AMOLED), flexible display, or the like. In some embodiments, the display unit 130 formed as a touch screen can also perform the function of the input unit 140.

The input unit 140 can receive various kinds of information from a user and create a corresponding input signal. The input unit 140 can have a plurality of input keys and function keys for setting various functions. For example, the functions keys can have navigation keys, side keys, or shortcut keys. Additionally, the input unit 140 can create a signal associated with a user setting or a function control and then transmit the signal to the control unit 110. The input unit 140 can be formed of at least one of a ball joystick, an optical joystick, a wheel key, a touch key, a touch pad, and a touch screen, or any combination thereof. In embodiments, the input unit 140 can create an input signal for turning on or off (or enabling or disabling) a foreign matter removal mode, an input signal for requesting the removal of foreign matter, an input signal for turning on or off (or activating or inactivating) the environmental sensor 171, etc. and then transmit the created input signal to the control unit 110.

The interface unit 150 can receive a cable for connection with any external device. For example, the interface unit 150 can be a connector suitable for Universal Serial Bus (USB) or micro USB standard, an ear jack connector, or the like. Embodiments are not limited to this, and the interface unit 150 can be formed of any other connector suitable for various standards.

The audio processing unit 160 can be connected with a speaker (SPK) 161 for outputting a received audio signal, an audio signal associated with an audio file stored in the memory unit 120, etc. and a microphone (MIC) 162 for sensing a user's voice or any other audio signal. In embodiments, the audio processing unit 160 can output, through the speaker 161, various sound effects in connection with the operation of the electronic device 1. For example, the audio processing unit 160 can output sound effects for indicating completion of measurement by the environmental sensor 171 or indicating completion of removal of foreign matter.

When air flows in the opening part, the audio processing unit 160 can detect a sound of the inflow of air through the microphone 162 and then transmit it to the control unit 110. In this case, the control unit 110 can automatically activate the environmental sensor 171.

The sensor unit 170 can include the environmental sensor 171 and a motion sensor 173. The environmental sensor 171 can measure environmental information about the surroundings of the electronic device 1. For example, the environmental sensor 171 can include a temperature sensor, a humidity sensor, an odorant sensor, a gas sensor, or the like. The motion sensor 173 can detect a motion of the electronic device 1. For example, the motion sensor 173 can detect that a user moves the electronic device 1 in any direction. When any movement of the electronic device 1 is detected (for example, when a user shakes the electronic device so as to accelerate the inflow of air), the motion sensor 173 can transmit a sensing value corresponding to the detected movement to the control unit 110. Then the control unit 110 can recognize a motion pattern and, if the recognized pattern is identical to a predefined motion pattern, automatically activate the environmental sensor 171.

In an alternative embodiment, if the received sensing value is greater than a given value (for example, in case an acceleration value of the electronic device 1 is greater than a given value), the control unit 110 can automatically activate the environmental sensor 171.

In some embodiments, when a movement of the electronic device 1 is detected, the control unit 110 can further check whether the inflow of air is detected through the microphone 162.

The memory unit 120 can store therein various programs or applications, including an operating system (OS), required for essential or optional functions of the electronic device 1, such as a sound reproduction function, an image viewer function, a video playback function, an internet access function, a text message function, a map service function, and the like. Additionally, the memory unit 120 can store therein various data, e.g., video data, game data, music data, movie data, map data, and the like. In various embodiments, the memory unit 120 can store therein a program designed for the operation of the environmental sensor 171. For example, if a motion of the electronic device 1 is detected through the motion sensor 173, and if the detected motion corresponds to a predefined motion pattern, this program stored in the memory unit 120 can activate the speaker 161 so as to control the removal of foreign matter from the surroundings of the environmental sensor 171 and from the inside of the duct.

The control unit 110 can control general operations of the electronic device 1 and flows of signals between internal blocks of the electronic device 1, and can also perform a function to process data. For example, the control unit 110 can be formed of a central processing unit (CPU), an application processor (AP), and the like. For example, the control unit 110 can be formed as a single core processor or a multi-core processor. The control unit 110 can control a process for the operation of the environmental sensor 171 (e.g., turn-on/off of the environmental sensor, turn-on/off of a foreign matter removal mode, etc.). A detailed description about the control unit 110 will be given below.

Although not illustrated in FIG. 14, the electronic device 1 can selectively further include elements for providing additional functions, such as a broadcast receiving module, a camera module, a digital sound playback module such as an MP3 module, a voice recognition module, and the like. According to a digital convergence tendency today, such elements can be varied, modified and improved in various ways, and any other elements equivalent to the above elements can be additionally or alternatively equipped in the electronic device 1. As will be understood by those skilled in the art, some of the above-mentioned elements in the electronic device 1 can be omitted or replaced with another.

Figure 15:
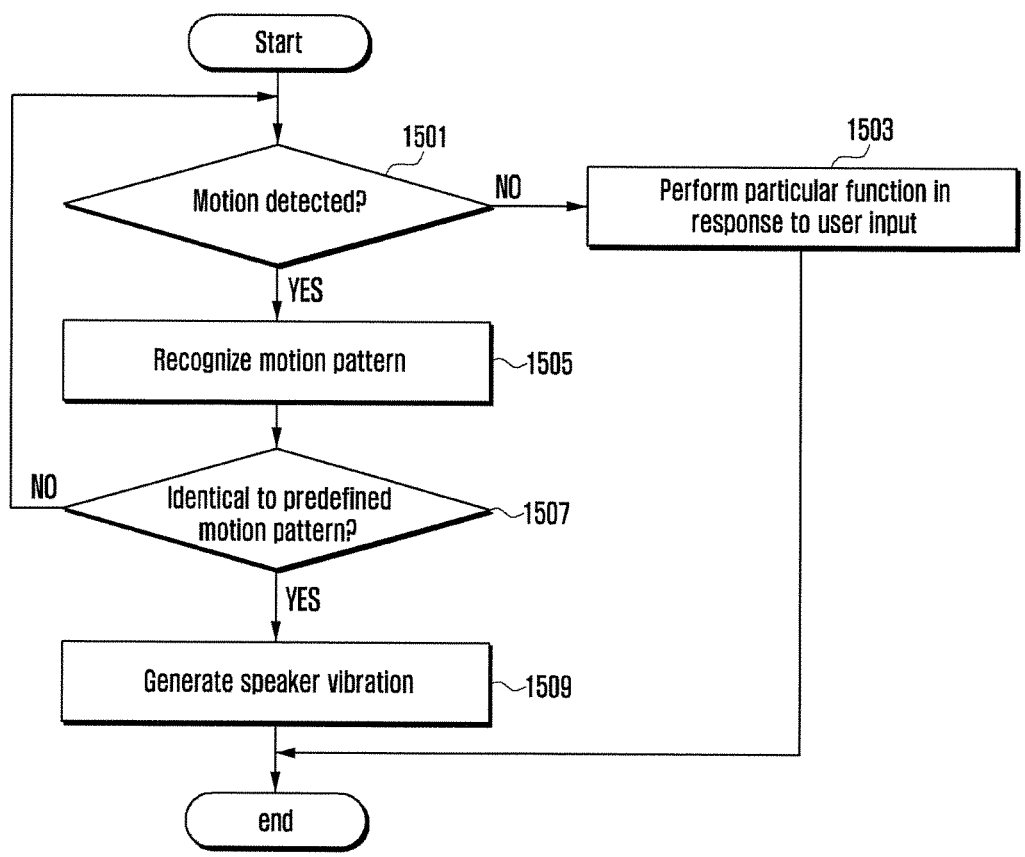
FIG. 15 is a flow diagram illustrating a method for removing foreign matter in accordance with various embodiments of the present disclosure.

FIG. 15 is a flow diagram illustrating a method for removing foreign matter in accordance with various embodiments of the present disclosure.

Referring to FIG. 15, at operation 1501, the control unit 110 of the electronic device 1 can check whether a motion of the electronic device 1 is detected. If no motion of the electronic device 1 is detected at operation 1501, the control unit 110 can perform a particular function in response to a user input at operation 1503. For example, the control unit 110 can perform a music playback function, an internet access function, a video recording function, etc. at a user's request, or maintain an idle state.

If any motion of the electronic device 1 is detected at operation 1501, the control unit 110 can recognize a motion pattern of the electronic device 1 at operation 1505. When the recognition of a motion pattern is completed, the control unit 110 can check at operation 1507 whether the recognized motion pattern is identical to a predefined motion pattern.

If the recognized motion pattern is not identical to the predefined motion pattern, the control unit 110 can return to the above-discussed operation 1501 and then perform subsequent operations. If the recognized motion pattern is identical to the predefined motion pattern, the control unit 110 can generate a vibration of the speaker 161 at operation 1509. This vibration of the speaker 161 can be generated for a predetermined time. As discussed above, the vibration of the speaker 161 can cause the flow of air, and this air flow can remove foreign matter from the inside of the electronic device 1.

Although it is described above that the control unit 110 generates a vibration of the speaker 161 just when a specific motion of the electronic device 1 predefined for the removal of foreign matter is detected through the motion sensor 173, this is exemplary only. Alternatively, when a specific motion predefined for a foreign matter removal is detected, the control unit 110 can output a popup window showing a query about whether to generate a vibration of the speaker 161 and then, depending on a user's selection, determine whether to generate such a vibration.

Additionally, although it is described above that the speaker is immediately activated in response to the detection of a predefined motion of the electronic device 1, other embodiments are also possible. For example, it is possible to offer a menu for turning on/off a foreign matter removal mode using the speaker and to control the speaker to be turned on in response to a menu selection.

Additionally, although the above discussion is focused on a foreign matter removal using the speaker 161, any foreign matter removing unit 190 can be separately used in various embodiments. Specifically, the foreign matter removing unit 190 can be a device that is turned on/off under the control of the control unit 110 and has the ability to cause the flow of air. For example, the foreign matter removing unit 190 can be the vibration motor or the DCJ which is previously described in FIGS. 10 and 11.

Meanwhile, the electronic device according to various embodiments can have an anti-fouling or anti-microbial coating on the duct in order to prevent any internal contamination.

Hereinbefore, a method for automatically activating a foreign matter removal mode is described. However, the electronic device according to some embodiment can automatically activate the environmental sensor 171 when a predefined motion is detected. Alternatively or additionally, the electronic device according to some embodiment can automatically activate the environmental sensor 171 when a sound associated with the inflow of outside air is detected through the microphone 162. Meanwhile, when an analysis about external environment is completed through the environmental sensor 171, the electronic device can automatically perform a foreign matter removal mode.

Figure 16:
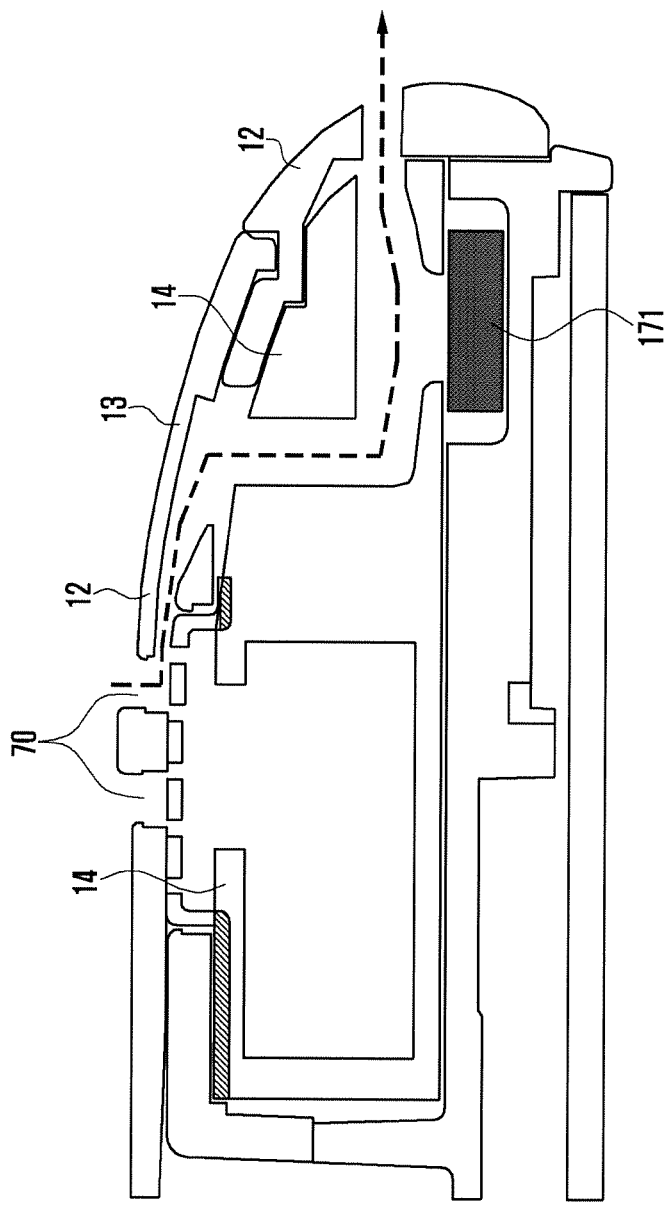
FIG. 16 is a cross-sectional view illustrating a duct structure of an electronic device in accordance with various embodiments of the present disclosure.

FIG. 16 is a cross-sectional view illustrating a duct structure of an electronic device in accordance with various embodiments of the present disclosure.

Referring to FIG. 16, the electronic device according to various embodiments can have the duct underneath the second and third cases 12 and 13. For example, the second and third cases 12 and 13 can be combined with each other such that a certain space remains between the second and third cases 12 and 13. This space can be used as the duct. In comparison with the above-discussed embodiment of FIG. 4 in which the duct is formed in the carrier 14, this embodiment can increase a mounting space for the speaker 161. This can minimize the degradation of performance of the speaker 161 due to a reduced mounting space of the speaker 161.

Figure 17A:
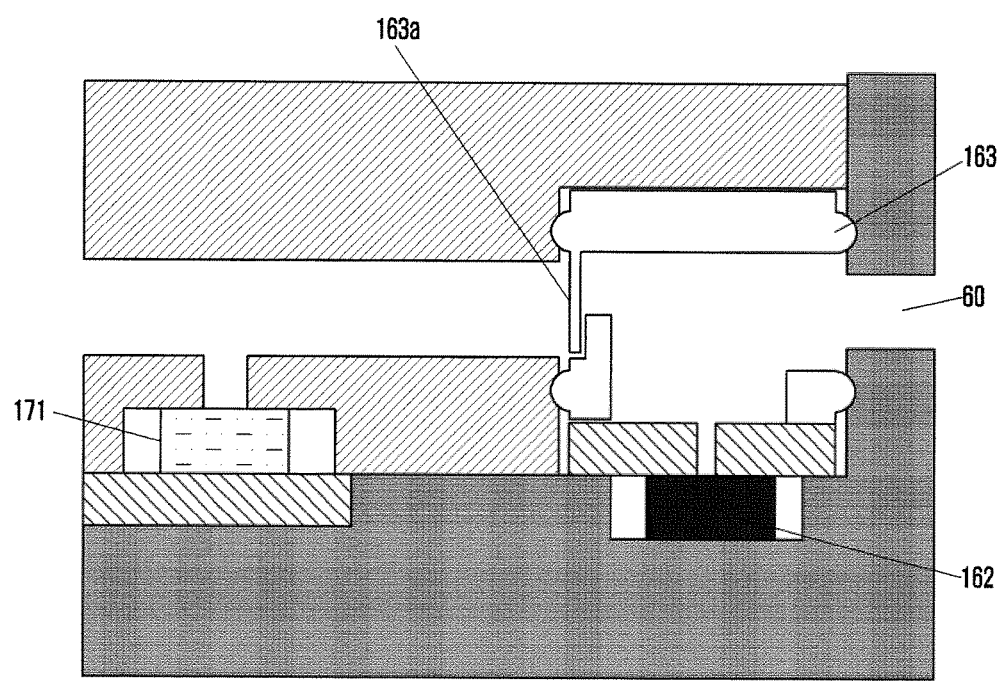
FIGS. 17A and 17B are cross-sectional views illustrating a duct structure of an electronic device in accordance with various embodiments of the present disclosure.
Figure 17B:
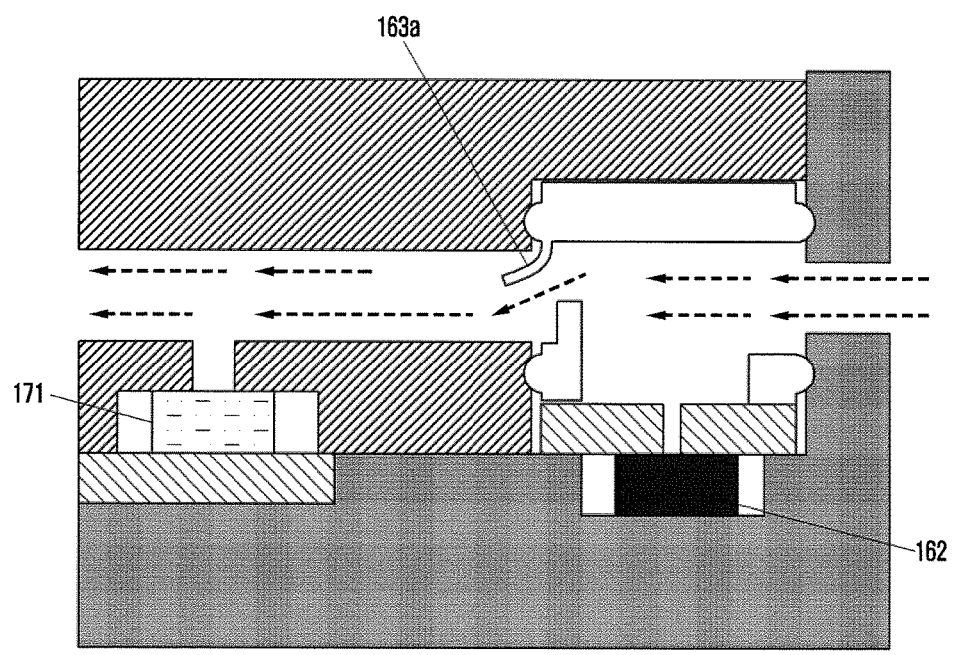

FIGS. 17A and 17B are cross-sectional views illustrating a duct structure of an electronic device in accordance with various embodiments of the present disclosure.

Referring to FIGS. 17A and 17B, the electronic device according to various embodiments can have a microphone holder 163 for protecting the microphone 162. Particularly, the microphone holder 163 can have a shield 163a disposed between the microphone 162 and the environmental sensor 171. The shield 163a can block the leakage or inflow of sound (e.g., howling) between the microphone 162 and the environmental sensor 171. Also, the shield 163a can block a slow air flow having a smaller speed than a given speed and pass a fast air flow having a greater speed than a given speed. For example, when any air flow occurs with a smaller speed than a given speed, the shield 163a can maintain a block state. If any air flow has a greater speed than a given speed, the shield 163a can be opened. This embodiment can prevent the degradation of performance of the microphone 162 due to a frequent inflow of air caused by an open state of the duct.

Figure 18:
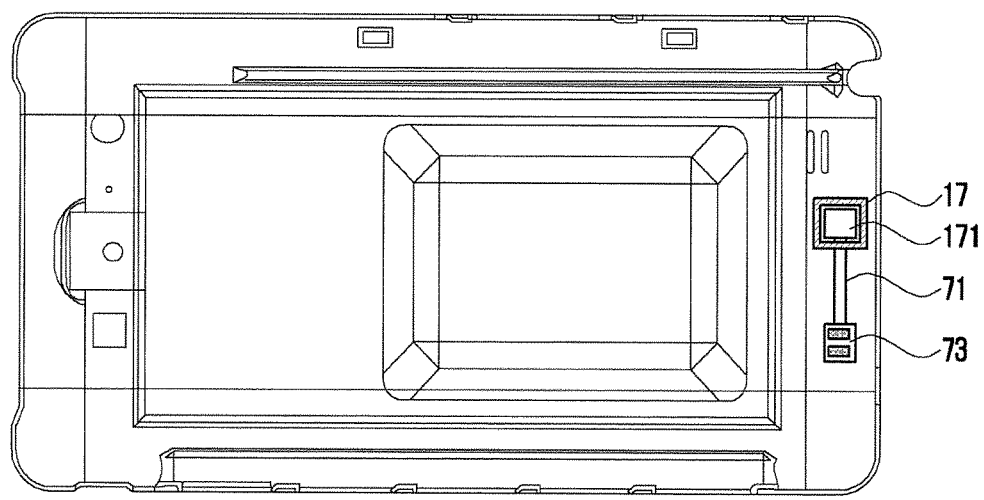
FIG. 18 is a schematic view illustrating an example of an environmental sensor mounted on the third case of an electronic device in accordance with various embodiments of the present disclosure.
Figure 19:
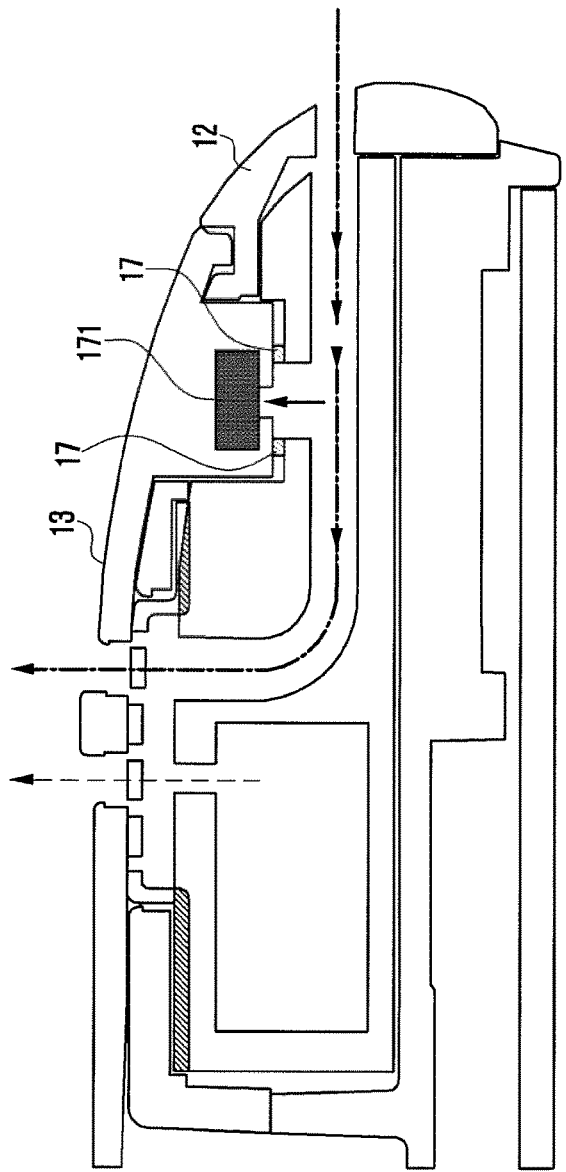
FIG. 19 is a cross-sectional view illustrating a duct structure of an electronic device fastened to the third case shown in FIG. 18 in accordance with various embodiments of the present disclosure.

FIG. 18 is a schematic view illustrating an example of an environmental sensor mounted on the third case of an electronic device in accordance with various embodiments of the present disclosure. FIG. 19 is a cross-sectional view illustrating a duct structure of an electronic device fastened to the third case shown in FIG. 18 in accordance with various embodiments of the present disclosure.

Referring to FIGS. 18 and 19, in the electronic device according to various embodiments, the environmental sensor 171 can be mounted on the third case 13. According to an embodiment, the environmental sensor can be mounted in the form of module on the third case 13. The environmental sensor module can include the environmental sensor 171, an FPCB (Flexible Printed Circuit Board) 71, and an interface 73. The environmental sensor 171 can be mounted on the inside of the third case 13 through inserted injection molding, for example. The third case 13 can have a sealing part 17 at a mounting area for the environmental sensor 171. The sealing part 17 can be mounted to cover the environmental sensor 171 such that the environmental sensor 171 can not be affected by external environments. The sealing part 17 can be formed of elastic material such as silicone, rubber, or the like.

When the second and third cases 12 and 13 are combined with each other, the environmental sensor 171 can be connected to the control unit 110, receive electric power, transmit and receive sensing signals and control signals through the interface 73, e.g., contact terminals. Although FIG. 18 shows two terminals of the interface 73, this is exemplary only. Alternatively, the interface 73 can have three or more terminals.

FIG. 19 shows a state in which the third case 13 is combined with the second case 12. Referring to FIG. 19, when a user blows air, a flowing air as indicated by an arrow can be partially supplied to the environmental sensor 171 mounted on the third case 13. The sealing part 17 can prevent air, flowing in through the duct, from leaking out through a gap between the second and third cases 12 and 13. Further, the sealing part 17 can prevent any air, other than the outside air flowing in through the duct, from being supplied to the environmental sensor 171.

Except that the environmental sensor 171 is located at the third case 13, the structure shown in FIG. 19 is similar to the above-discussed structure shown in FIG. 4. Therefore, a description about similar elements will be omitted. As understood by those skilled in the art, the above-discussed embodiments shown in FIGS. 7 to 17B can be also applied to this embodiment shown in FIGS. 18 and 19.

In an alternative embodiment, a plurality of third cases having different types of environmental sensors mounted thereon can be offered. For example, the respective third cases can be used for the odorant sensor, the temperature sensor, and the humidity sensor. For example, a user who desires to measure temperature can attach the third case 13 having the temperature sensor mounted thereon to the electronic device, and similarly a user who desires to measure humidity can attach the third case 13 having the humidity sensor mounted thereon to the electronic device. Namely, a user can easily measure desired environmental information by selectively using many cases.

Figure 20:
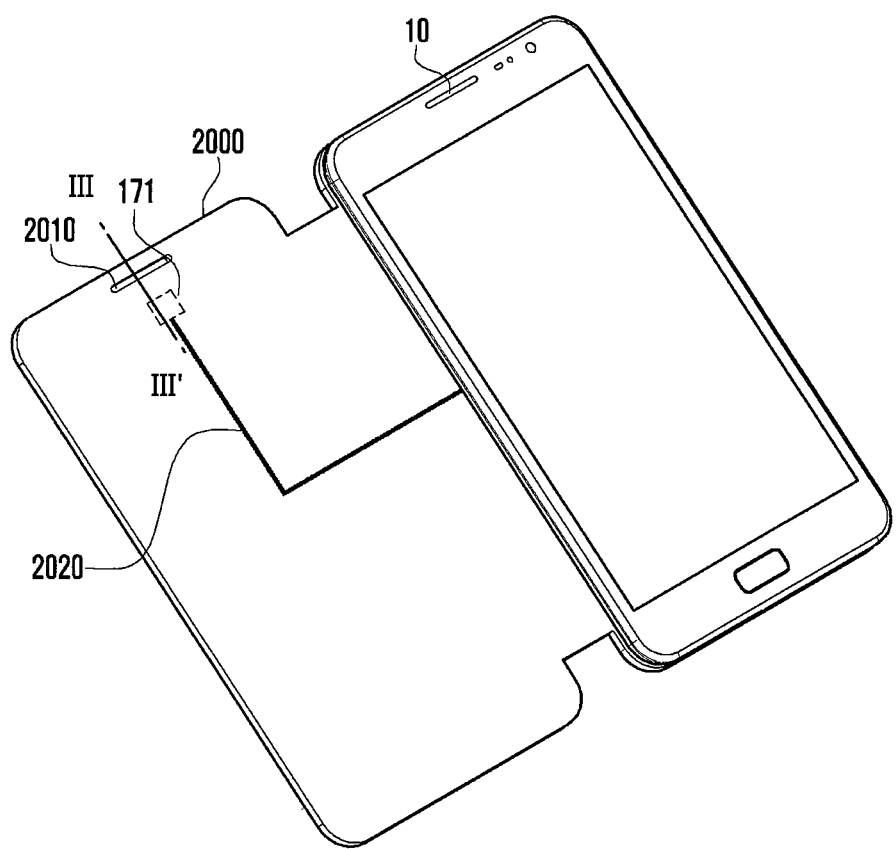
FIG. 20 is a perspective view illustrating an electronic device having an environmental sensor mounted on a front flip cover being in an open state in accordance with various embodiments of the present disclosure.
Figure 21:
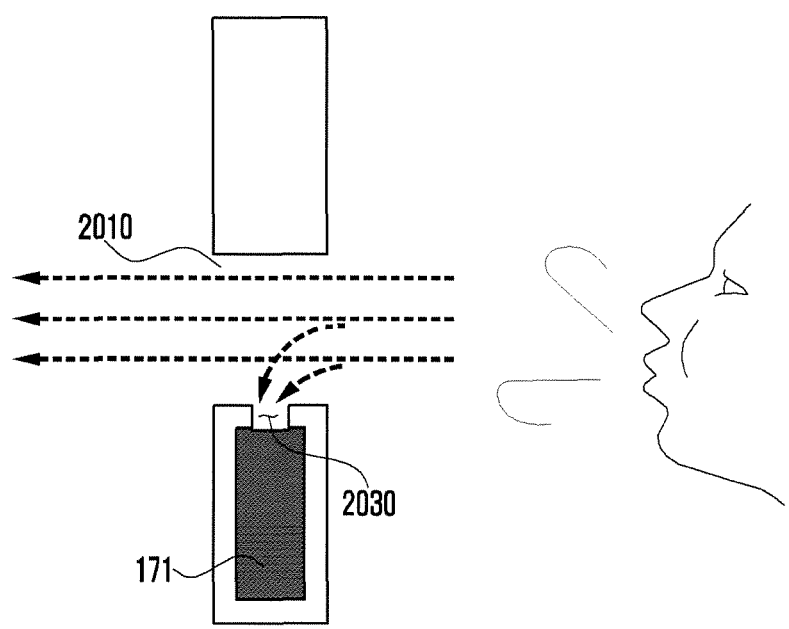
FIG. 21 is a cross-sectional view taken along the line C-C' in FIG. 20.

FIG. 20 is a perspective view illustrating an electronic device having an environmental sensor mounted on a front flip cover being in an open state in accordance with various embodiments of the present disclosure. FIG. 21 is a cross-sectional view taken along the line C-C' in FIG. 20.

Referring to FIGS. 20 and 21, the environmental sensor 171 can be mounted on the front flip cover 2000 which is detachably combined with the electronic device. For example, as shown in FIG. 20, the environmental sensor 171 can be mounted near a hole 2010 formed at an upper part of the front flip cover 2000. This hole 2010 can correspond to the receiver 10, for example.

The front flip cover 2000 can have a plurality of interfaces 2020, e.g., wiring, formed on the inner surface thereof and designed for signal transmission (e.g., communication) and power supply between the environmental sensor 171 and the control unit 110. The interfaces 2020 can be formed of at least one of a wireless interface and a wired interface. For example, using contact terminals as earlier discussed in FIGS. 18 and 19, the interfaces 2020 can be electrically coupled to a PCB (not shown) of the electronic device.

Referring to FIG. 21 which is a cross-sectional view taken along the line C-C' in FIG. 20, a duct 2030 can be formed between the environmental sensor 171 and the hole 2010 of the front flip cover 2000. When a user blows air toward the hole 2010 in an open state of the front flip cover 2000, part of air passing through the hole 2010 can be supplied to the environmental sensor 171 through the duct 2030.

In some embodiment, the control unit 110 can be mounted on the front flip cover 2000. In this case, the interfaces 2020 can have an interface for a power supply or an interface for an electric connection between the control unit 110 and electronic components embedded in the electronic device.

Figure 22:
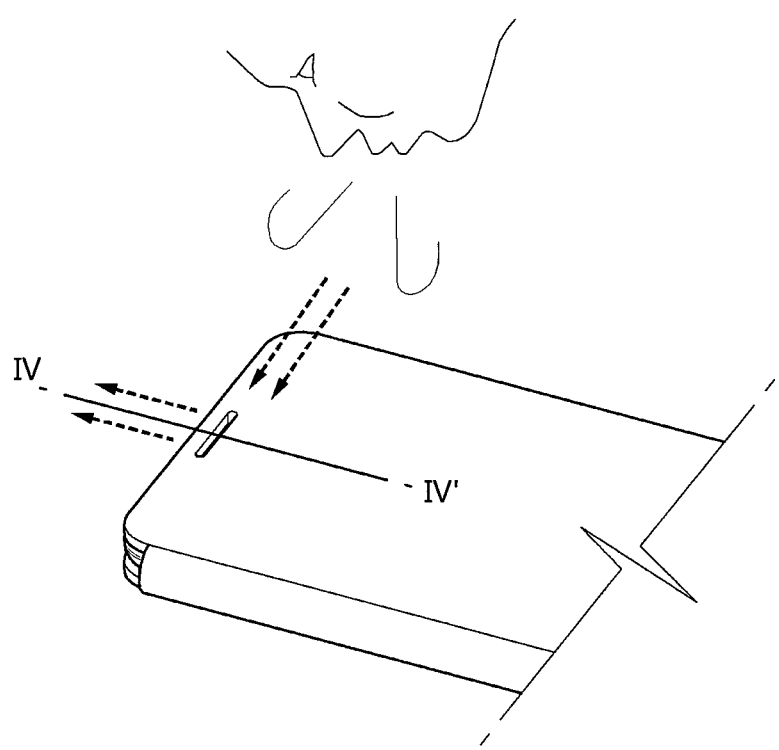
FIG. 22 is a perspective view illustrating an electronic device having an environmental sensor mounted on a front flip cover being in a closed state in accordance with various embodiments of the present disclosure.
Figure 23:
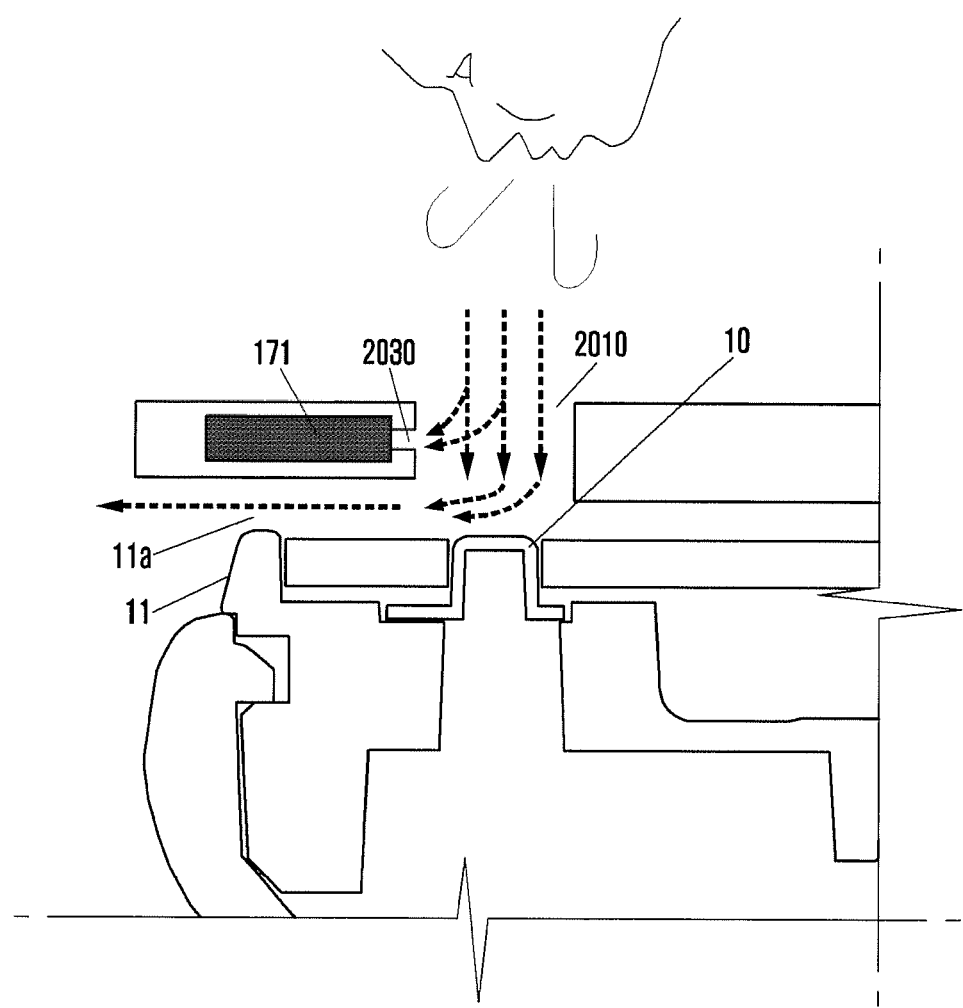
FIG. 23 is a cross-sectional view taken along the line D-D' in FIG. 22.

FIG. 22 is a perspective view illustrating an electronic device having an environmental sensor mounted on a front flip cover being in a closed state in accordance with various embodiments of the present disclosure. FIG. 23 is a cross-sectional view taken along the line D-D' in FIG. 22.

Referring to FIGS. 22 and 23, a user can measure environmental information even in a closed state of the front flip cover. For this, the first case 11 of the electronic device can have a groove 11a formed therein. The groove 11a can be formed intentionally. Alternatively, the groove 11a can be a gap naturally formed between the front flip cover and the first case 11.

When a user blows air toward the hole 2010 of the front flip cover, part of air passing through the hole 2010 can be supplied to the environmental sensor 171 through the duct 2030. The other part of air can flow out through the groove 11a.

In this embodiment, the environmental sensor 171 is formed on the front flip cover. However, the environmental sensor 171 can be also formed on other various accessories to be used for the electronic device.

Additionally, instead of the groove 11a discussed in this embodiment, a certain hole or the like can be formed in the first case 11 in various embodiments.

Figure 24:
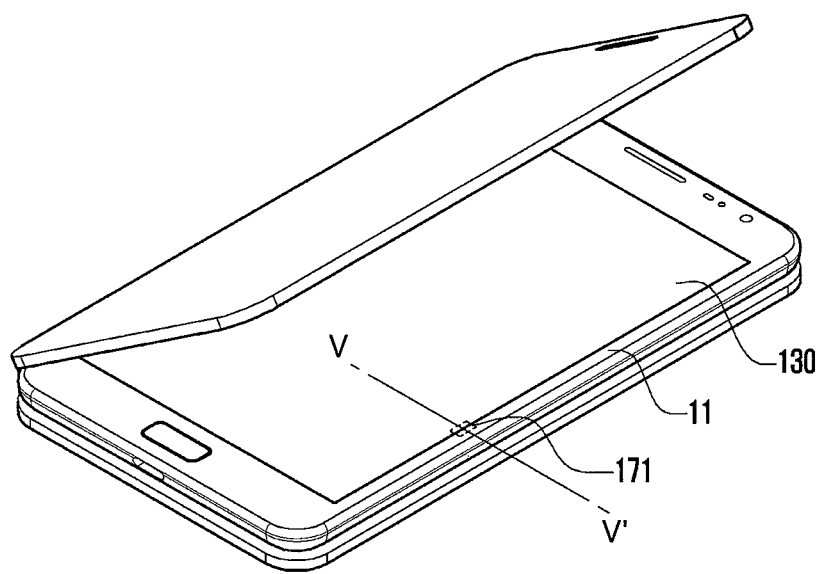
FIG. 24 is a perspective view illustrating an electronic device having an environmental sensor mounted on a front side thereof in accordance with various embodiments of the present disclosure.
Figure 25:
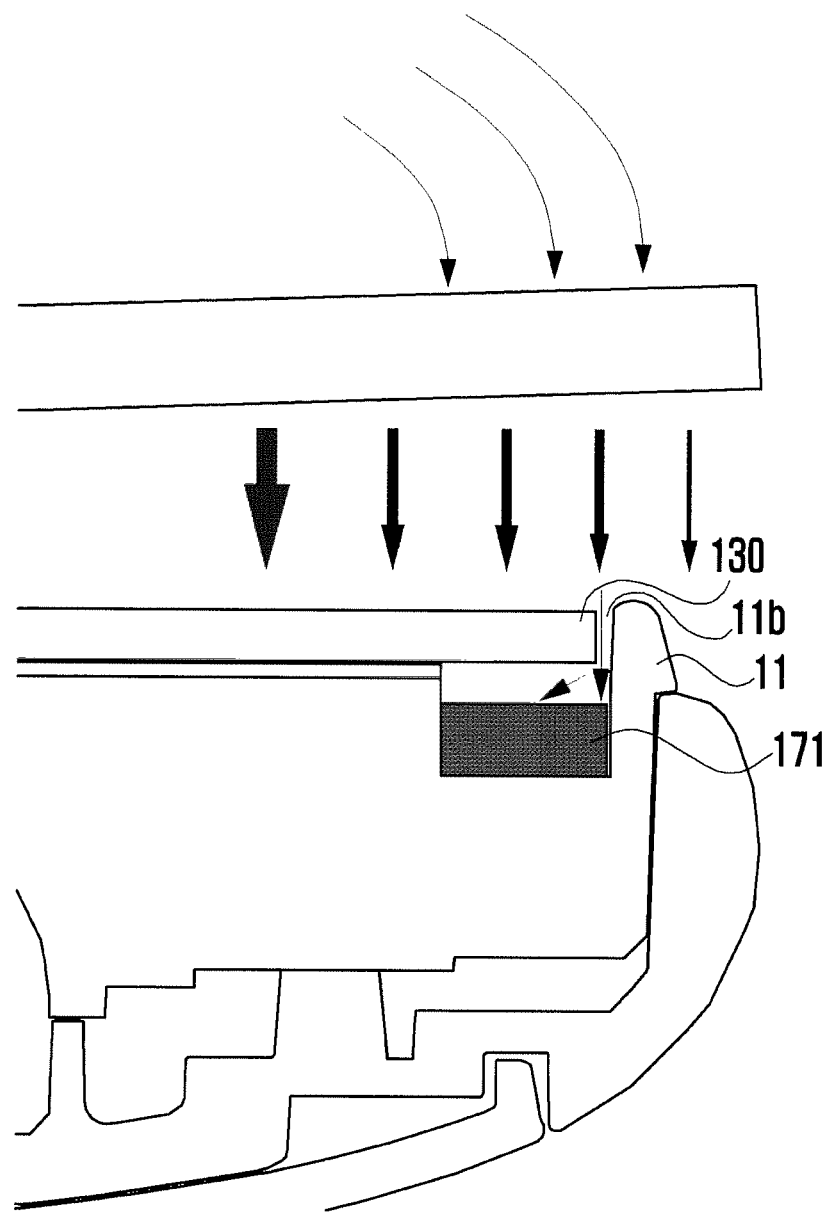
FIGS. 25 and 26 are cross-sectional views taken along the line E-E' in FIG. 24.
Figure 26:
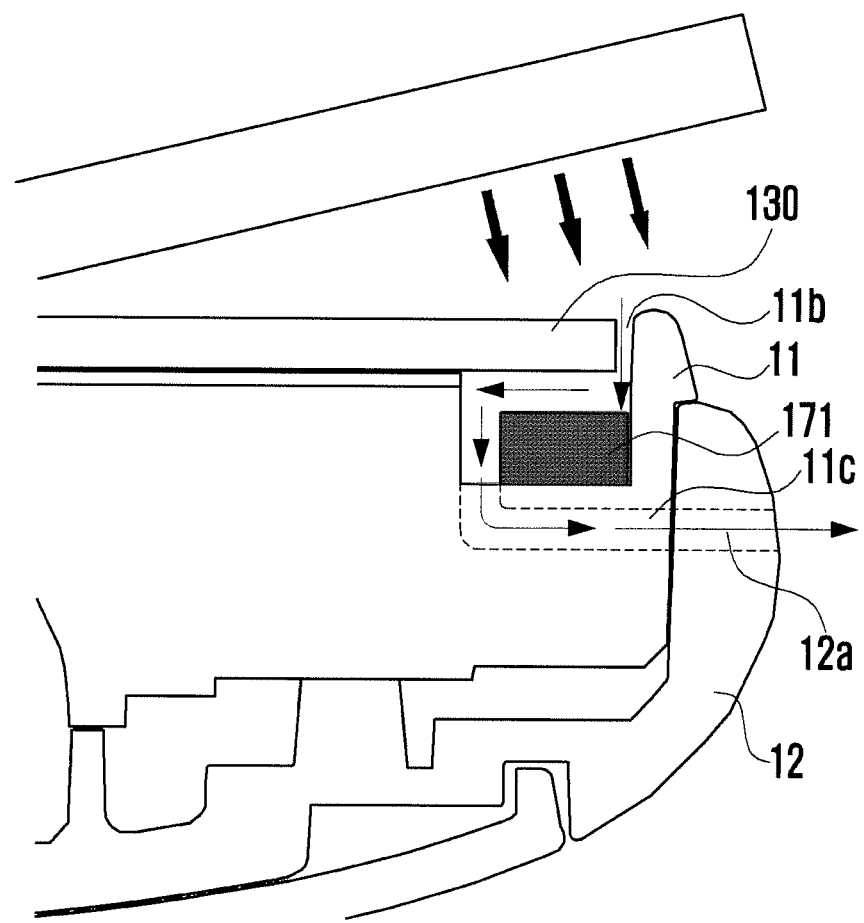

FIG. 24 is a perspective view illustrating an electronic device having an environmental sensor mounted on a front side thereof in accordance with various embodiments of the present disclosure. FIGS. 25 and 26 are cross-sectional views taken along the line E-E' in FIG. 24.

Referring to FIGS. 24 to 26, the environmental sensor 171 can be mounted on the front side of the electronic device. For example, as shown in FIG. 24, the environmental sensor 171 can be embedded in a right edge (e.g., a boundary between the display unit 130 and the first case 11) of the electronic device.

First, referring to FIG. 25, by a wind occurring when the front flip cover is closed, the outside air can flow in the environmental sensor 171 through a gap 11b between the display unit 130 and the first case 11. Like this, since the environmental sensor 171 is formed below the gap 11b between the display unit 130 and the first case 11, the outside air can be effectively supplied to the environmental sensor 171 whenever the front flip cover is opened or closed. Additionally, the utilization of the gap 11b which is normally formed between the display unit 130 and the first case 11 can require no separate duct and also allow a freer design of the electronic device.

Next, referring to FIG. 26, the first and second cases 11 and 12 can have the first and second ducts 11c and 12a, respectively, designed for exhausting air flowing in through the gap 11b. In this case, by a wind occurring when the front flip cover is closed, the outside air can flow in the environmental sensor 171 through the gap 11b between the display unit 130 and the first case 11, and then the air can flow out through the first and second ducts 11c and 12a.

Although FIG. 26 shows that the first and second ducts 11c and 12a are formed in the first and second cases 11 and 12, the first and second ducts 11c and 12a can be formed in the first case 11 only in another embodiment.

Additionally, although the above discussion is focused on the gap 11*b* between the display unit 130 and the first case 11, another gap between the home key 42 and the display unit 130 can be used as an inflow hole for the outside air.

As fully discussed hereinbefore in various embodiments, the electronic device having the environmental sensor and the operation method thereof can reduce time required for detecting external environmental information and also enhance the accuracy of such a detection. For example, according to various embodiments, it is possible for the environmental sensor to exactly and promptly detect external environmental information through a suitable substructure (e.g., an opening part) which allows an air inflow.

The above-discussed method is described herein with reference to flowchart illustrations of user interfaces, methods, and computer program products according to embodiments of the present disclosure. It will be understood that each block of the flowchart illustrations, and combinations of blocks in the flowchart illustrations, can be implemented by computer program instructions. These computer program instructions can be provided to a processor of a general purpose computer, special purpose computer, or other programmable data processing apparatus to produce a machine, such that the instructions, which are executed via the processor of the computer or other programmable data processing apparatus, create means for implementing the functions specified in the flowchart block or blocks. These computer program instructions can also be stored in a computer usable or computer-readable memory that can direct a computer or other programmable data processing apparatus to function in a particular manner, such that the instructions stored in the computer usable or computer-readable memory produce an article of manufacture including instruction means that implement the function specified in the flowchart block or blocks. The computer program instructions can also be loaded onto a computer or other programmable data processing apparatus to cause a series of operational steps to be performed on the computer or other programmable apparatus to produce a computer implemented process such that the instructions that are executed on the computer or other programmable apparatus provide steps for implementing the functions specified in the flowchart block or blocks.

And each block of the flowchart illustrations may represent a module, segment, or portion of code, which comprises one or more executable instructions for implementing the specified logical function(s). It should also be noted that in some alternative implementations, the functions noted in the blocks may occur out of the order. For example, two blocks shown in succession may in fact be executed substantially concurrently or the blocks may sometimes be executed in the reverse order, depending upon the functionality involved.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A mobile electronic device comprising:
at least one environmental sensor configured to detect an environmental information with respect to outside of the mobile electronic device;
a first opening and a second opening formed through a body of the mobile electronic device, the first opening and the second opening providing passage for air from an exterior to enter the mobile electronic device;
a microphone to detect, via the first opening, a sound with respect to the outside of the mobile electronic device;
a duct formed between the first opening and the second opening, the duct connecting the at least one environmental sensor, the microphone and the first opening and the second opening,
wherein the microphone is located fully within an interior of the duct;
a first case on which a display unit is mounted; a second case combined with the first case and the duct connected to the first opening and the second opening; and
a third case connected functionally to the body of the mobile electronic device and including at least one hole, wherein the at least one environmental sensor is associated with the third case and is configured to detect outside air which flows in through the first opening and the second opening and the duct.

2. The mobile electronic device of claim 1, wherein the duct has an internal space becoming broader toward a position of the at least one environmental sensor.

3. The mobile electronic device of claim 1, wherein the duct protrudes toward the at least one environmental sensor.

4. The mobile electronic device of claim 1, wherein the duct includes a bump.

5. The mobile electronic device of claim 1, further comprising: an auxiliary unit configured to accelerate air flow, the auxiliary unit comprising at least one of a fan using a vibration motor or dual piezoelectric cooling jets (DCJ).

6. The mobile electronic device of claim 1, wherein the first opening includes at least one of a protective member for preventing an inflow of a foreign matter or a receptacle configured to store the foreign matter.

7. The mobile electronic device of claim 1, further comprising: a foreign matter removing unit configured to remove foreign matter, the foreign matter removing unit configured to cause an outward air movement from the mobile electronic device.

8. The mobile electronic device of claim 1, wherein the first opening includes a microphone hole and the second opening is formed through the body of the mobile electronic device in a location of at least one of a speaker hole, an interface unit hole, a receiver hole, a gap between a display unit and a case, or an ear jack hole.

9. The mobile electronic device of claim 1, further comprising a shield disposed between the microphone and the at least one environmental sensor and configured to block a leakage or inflow of sound.

10. The mobile electronic device of claim 1, wherein at least part of the duct is formed in a carrier in which a speaker is mounted.

11. The mobile electronic device of claim 1, further comprising: a sealing part located between the second and third cases and covering the at least one environmental sensor; and an interface configured to electrically couple the at least one environmental sensor and an electronic component in the body of the mobile electronic device.

* * * * *